United States Patent
Rondeau

(10) Patent No.: US 6,436,153 B2
(45) Date of Patent: *Aug. 20, 2002

(54) COMPOSITION FOR THE DIRECT DYEING OF KERATIN FIBRES WITH A CATIONIC DIRECT DYE AND A POLYOL AND/OR A POLYOL ETHER

(75) Inventor: Christine Rondeau, Sartrouville (FR)

(73) Assignee: L'Oréal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,890

(22) Filed: May 28, 1999

(30) Foreign Application Priority Data

May 28, 1998 (FR) .......................... 98 06751

(51) Int. Cl.[7] .................................. A61K 7/13
(52) U.S. Cl. ................ 8/426; 8/407; 8/429; 8/431; 8/609; 8/610; 8/611; 8/613; 8/654; 8/655; 8/657; 8/659
(58) Field of Search .................. 8/426, 405, 407, 8/429, 431, 609, 610, 611, 613, 654, 655, 657, 659

(56) References Cited

U.S. PATENT DOCUMENTS

| | | | |
|---|---|---|---|
| 2,983,651 A | * 5/1961 | Seemuller et al. | 8/426 |
| 3,482,923 A | * 12/1969 | Boosen et al. | 8/426 |
| 3,578,386 A | * 5/1971 | Kalopissis et al. | 8/426 |
| 3,632,290 A | * 1/1972 | Tucker et al. | 8/426 |
| 3,869,454 A | * 3/1975 | Lang et al. | 8/426 |
| 3,955,918 A | * 5/1976 | Lang | 8/426 |
| 3,985,499 A | 10/1976 | Lang et al. | 8/426 |
| 3,986,825 A | 10/1976 | Sokol | |
| 4,025,301 A | * 5/1977 | Lang | 8/426 |
| 4,151,162 A | 4/1979 | Lang et al. | 534/607 |
| 4,772,462 A | 9/1988 | Boothe et al. | |
| 4,781,723 A | 11/1988 | Gross et al. | |
| 5,393,305 A | 2/1995 | Cohen et al. | |
| 5,474,578 A | * 12/1995 | Chan et al. | 8/426 |
| 5,708,151 A | * 1/1998 | Mockli | 534/608 |
| 5,735,908 A | 4/1998 | Cotteret et al. | |
| 5,879,412 A | * 3/1999 | Rondeau et al. | 8/426 |
| 5,919,273 A | * 7/1999 | Rondeau et al. | 8/426 |
| 5,948,124 A | 9/1999 | Grit | |
| 5,993,490 A | * 11/1999 | Rondeau et al. | 8/426 |
| 6,001,135 A | * 12/1999 | Rondeau et al. | 8/426 |
| 6,007,585 A | 12/1999 | Syed et al. | |
| 6,312,677 B1 | 11/2001 | Millequant et al. | |

FOREIGN PATENT DOCUMENTS

| | | |
|---|---|---|
| DE | 3 829 870 | 4/1989 |
| EP | 0 557203 A1 | 8/1993 |
| EP | 0 714 954 | 6/1996 |
| EP | 0 850 636 | 7/1998 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 586 913 | 3/1987 |
| WO | WO 95/01772 | 1/1995 |
| WO | WO 95/15144 | 6/1995 |

OTHER PUBLICATIONS

English language Derwent Abstract of DE 3 829 870, Apr. 1989.
English language Derwent Abstract of EP 0 714 954, Jun. 1996.
English language Derwent Abstract of EP 0 850 636, Jul. 1998.
English language Derwent Abstract of Ep 0 850 637, Jul. 1998.
English language Derwent Abstract of EP 0 850 638, Jul. 1998.
English language Derwent Abstract of FR 2 189 006, Jan. 1974.
English language Derwent Abstract of FR 2 285 851, Apr. 1976.
English language Derwent Abstract of FR 2 140 205, Jan. 1973.
English language Derwent Abstract of FR 2 586 913, Mar. 1987.

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to a direct dye composition for keratin fibers, in particular for human keratin fibers such as the hair, comprising, in a medium which is suitable for dyeing and which is free of oxidases or oxidoreductases, at least one cationic direct dye of given formula and at least one specific polyol and/or polyol ether. Subjects of the invention are also the dyeing processes and devices/kits using the said composition.

60 Claims, No Drawings

COMPOSITION FOR THE DIRECT DYEING OF KERATIN FIBRES WITH A CATIONIC DIRECT DYE AND A POLYOL AND/OR A POLYOL ETHER

The invention relates to a direct dye composition for keratin fibres, in particular for human keratin fibres such as the hair, comprising, in a medium which is suitable for dyeing and which is free of oxidases or oxidoreductases, at least one cationic direct dye of given formula and at least one specific polyol and/or polyol ether.

Subjects of the invention are also the dyeing processes and devices using the said composition.

In the hair sector, semi-permanent or temporary dyeing, or direct dyeing, involves dyes capable of giving the hair's natural colour a more or less pronounced change which may withstand shampooing several times. These dyes are known as direct dyes; they can be used with or without an oxidizing agent. In the presence of an oxidizing agent, the aim is to obtain a lightening coloration. The lightening coloration is carried out by applying to the hair the mixture, prepared at the time of use, of a direct dye and an oxidizing agent, and in particular makes it possible to obtain, by lightening the melanin in the hair, an advantageous effect such as a uniform colour in the case of grey hair, or to bring out the colour in the case of naturally pigmented hair.

Among the cationic direct dyes available in the field of dyeing keratin fibres, in particular human keratin fibres, compounds which are already known are those whose structure is developed in the text which follows; nevertheless, these dyes lead to colorations which have properties that are still insufficient as regards the staying power, in terms of resistance to the various attacking factors to which the hair may be subjected (light, bad weather, shampooing).

After considerable research conducted in this matter, the Applicant has now discovered that it is possible to obtain novel compositions for the direct dyeing of keratin fibres, which are capable of leading to colorations which can be particularly resistant to the various attacking factors to which the hair may be subjected, by combining at least one specific polyol and/or polyol ether with at least one cationic direct dye known in the prior art, and of formulae respectively defined below.

This discovery forms the basis of the present invention.

A first subject of the present invention is thus a composition for the direct dyeing of keratin fibres, and in particular human keratin fibres such as the hair, containing, in a medium which is suitable for dyeing, (i) at least one cationic direct dye whose structure corresponds to the following formulae, characterized in that it also contains (ii) at least one specific polyol and/or polyol ether.

(i) The cationic direct dye which can be used according to the present invention is a compound chosen from those of formulae (I), (II), (III) and (III') below:

a) the compounds of formula (I) below:

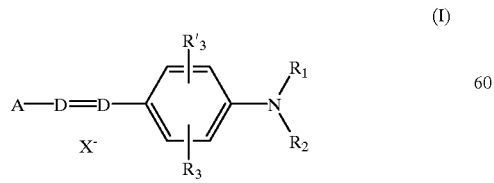

(I)

in which formula (I):

D is chosen from a nitrogen atom and a —CH group, $R_1$ and $R_2$, which may be identical or different, are chosen from a hydrogen atom, $C_1$–$C_4$ alkyl radicals optionally having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals, $R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, $X^-$ is an anion, preferably chosen from chloride, methyl sulphate, and acetate, A is a group chosen from structures $A_1$ to $A_{18}$ below:

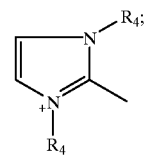

$A_1$

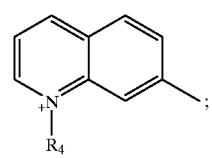

$A_2$

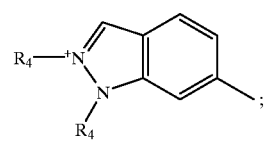

$A_3$

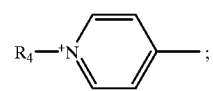

$A_4$

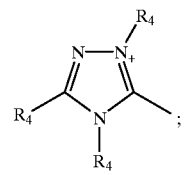

$A_5$

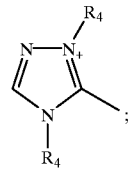

$A_6$

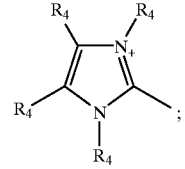

$A_7$

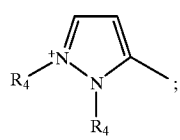 A8

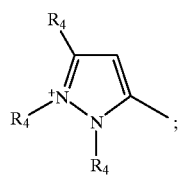 A9

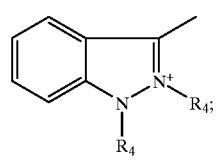 A10

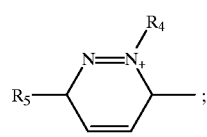 A11

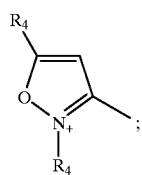 A12

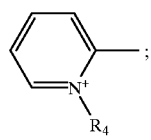 A13

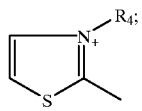 A14

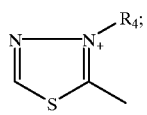 A15

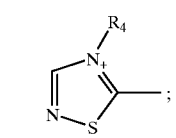 A16

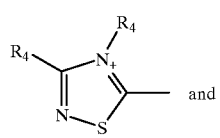 A17
and

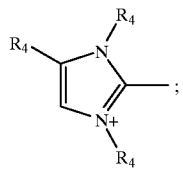 A18 in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

b) the compounds of formula (II) below:

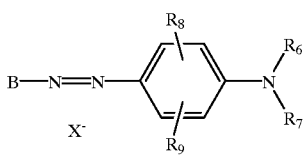

(II)

in which formula (II):

$R_6$ is chosen from a hydrogen atom and $C_1$–$C_4$ alkyl radicals, $R_7$ is chosen from a hydrogen atom, alkyl radicals having a substituent chosen from —CN and amino radicals, and a 4'-aminophenyl radical, or forms, with $R_6$, a nitrogenous heterocycle optionally oxygenated and optionally having a substituent chosen from $C_1$–$C_4$ alkyl radicals, $R_8$ and $R_9$, which may be identical or different, are chosen from a hydrogen atom, halogen atoms, such as bromine, chlorine, or fluorine, and $C_1$–$C_4$ alkyl, $C_1$–$C_4$ alkoxy, and —CN radicals, $X^-$ is an anion, B is a group chosen from structures B1 to B6 below:

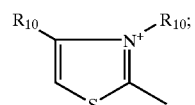 B1

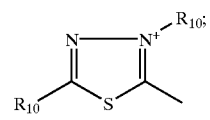 B2

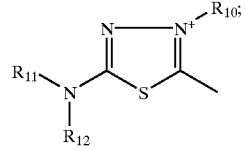 B3

-continued

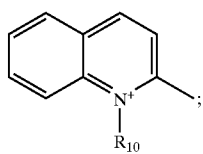
B4

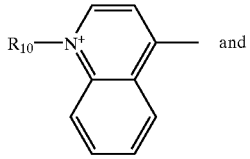
B5
and

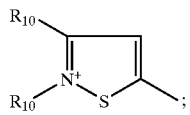
B6 in which $R_{10}$ is chosen from $C_1$–$C_4$ alkyl radicals, and $R_{11}$ and $R_{12}$, which may be identical or different, are chosen from a hydrogen atom and $C_1$–$C_4$ alkyl radicals;

c) the compounds of formulae (III) and (III') below:

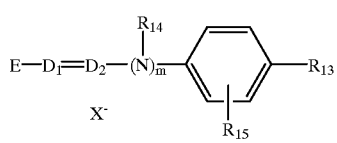
(III)

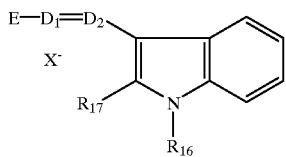
(III')

in which formulae (III) and (III'):
- $R_{13}$ is chosen from a hydrogen atom, $C_1$–$C_4$ alkoxy radicals, halogen atoms, such as bromine, chlorine, iodine and fluorine, and unsubstituted and substituted amino radicals,
- $R_{14}$ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals,
- $R_{15}$ is chosen from a hydrogen atom and halogen atoms, such as bromine, chlorine, iodine and fluorine,
- $R_{16}$ and $R_{17}$, which may be identical or different, are chosen from a hydrogen atom and $C_1$–$C_4$ alkyl radicals,
- $D_1$ and $D_2$, which may be identical or different, are chosen from a nitrogen atom and a —CH group,
- m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

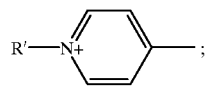
E1

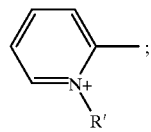
E2

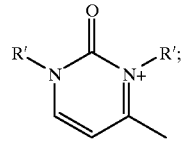
E3

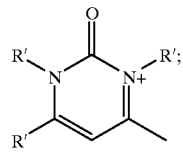
E4

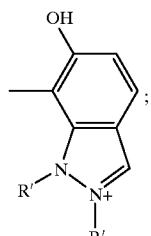
E5

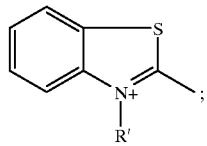
E6

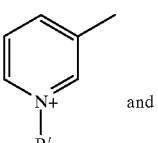
E7
and

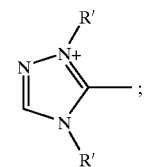
E8 in which R' is chosen from $C_1$–$C_4$ alkyl radicals;

when m is 0 and when $D_1$ is a nitrogen atom, then E can also be a group of structure E9 below:

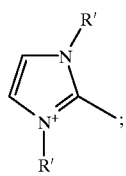

E9 in which R' is chosen from $C_1$–$C_4$ alkyl radicals.

The cationic direct dyes of formulae (I), (II), (III) and (III') which can be used in the dye compositions in accordance with the invention are known compounds and are described, for example, in patent applications WO 95/01772, WO 95/15144 and EP-A-0,714,954 (the disclosures of which are specifically incorporated by reference herein).

Among the cationic direct dyes of formula (I) which can be used in the dye compositions in accordance with the invention, mention may be made more particularly of the compounds corresponding to structures (I1) to (I52) below:

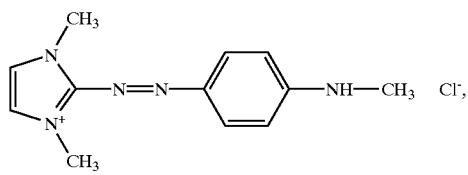
(I1)

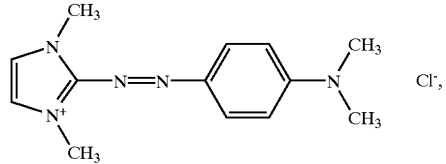
(I2)

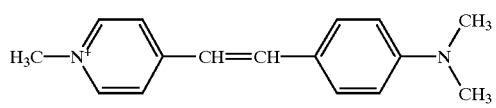
(I3)

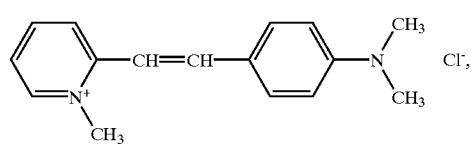
(I4)

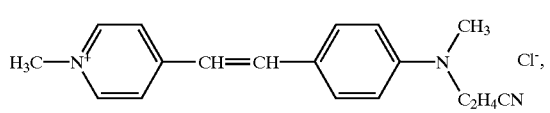
(I5)

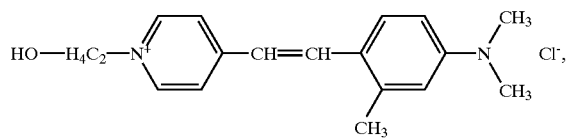
(I6)

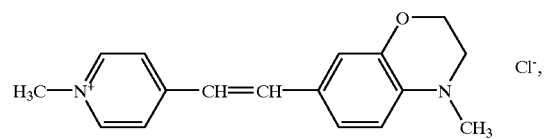
(I7)

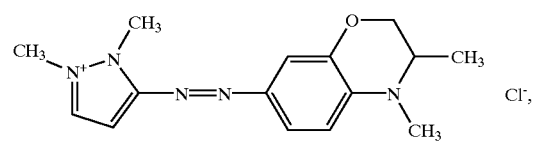
(I8)

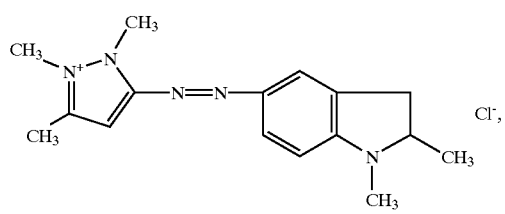
(I9)

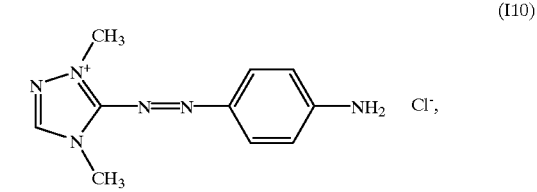
(I10)

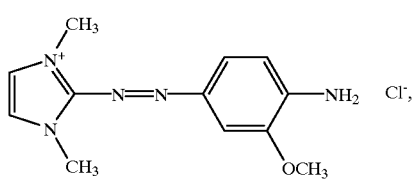
(I11)

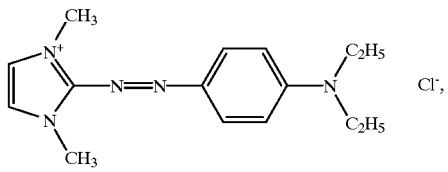
(I12)

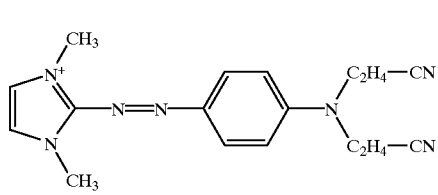
(I13)

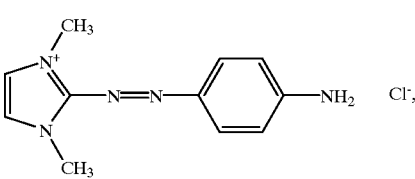
(I14)

(I15)
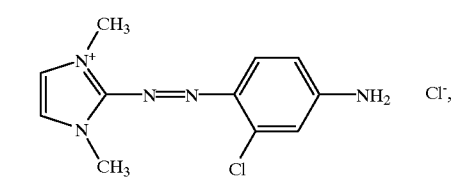
(I16)
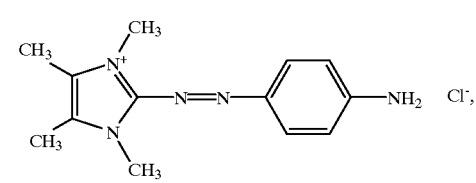
(I17)
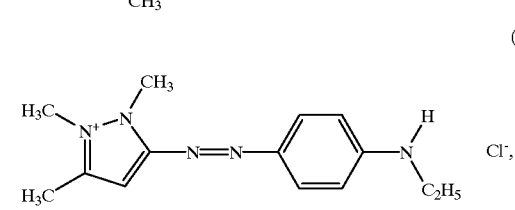
(I18)
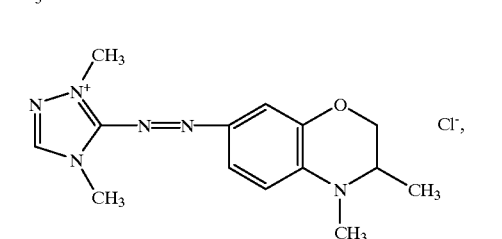
(I19)
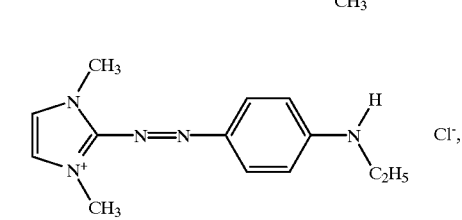
(I20)
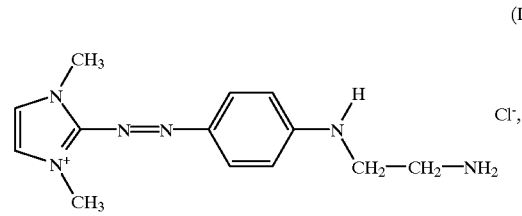
(I21)
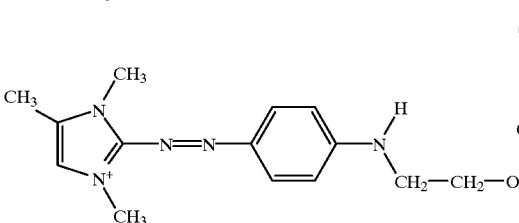
(I22)
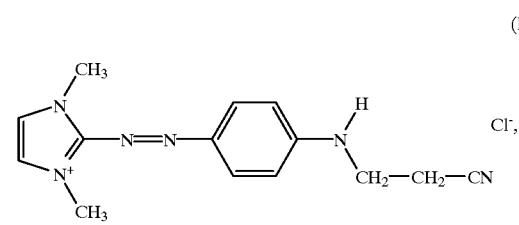
(I23)
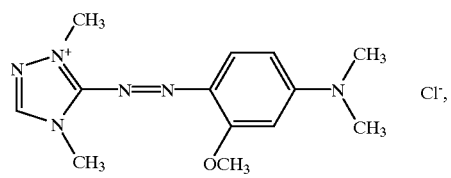
(I24)
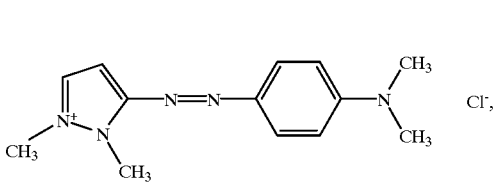
(I25)
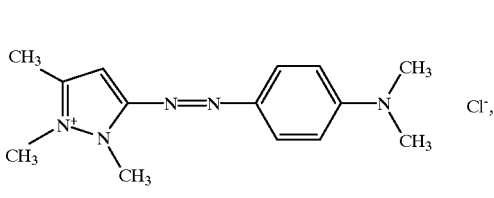
(I26)
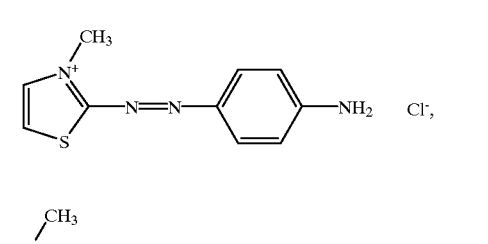
(I27)
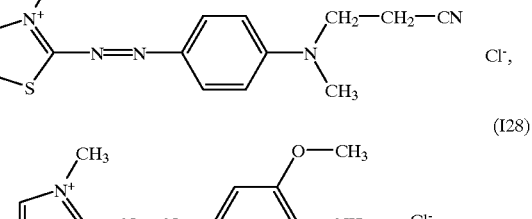
(I28)
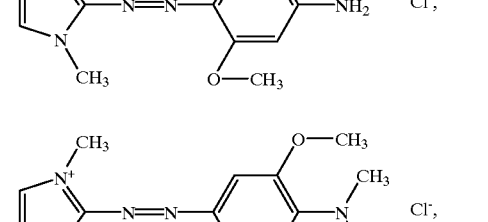
(I29)
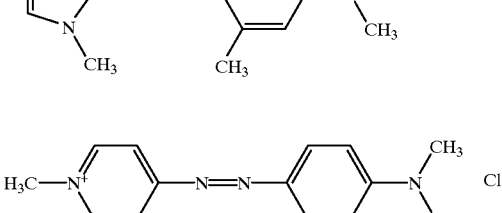
(I30)
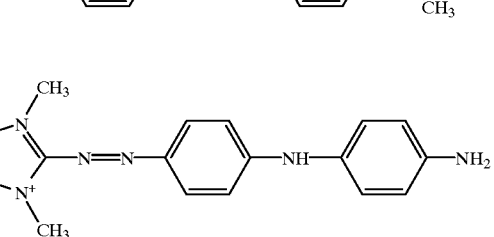
(I31)
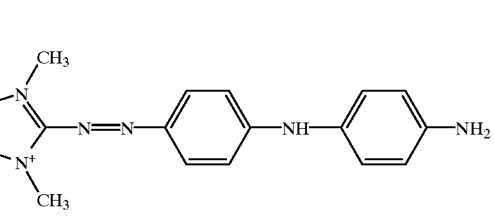

-continued
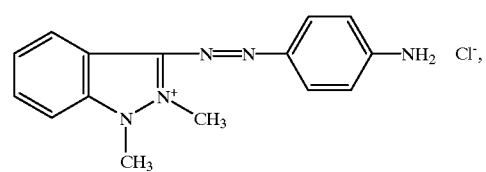 (I32) Cl⁻,
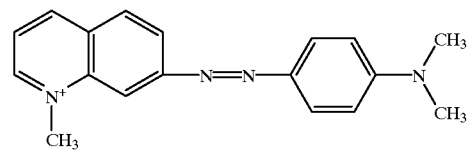 (I33) Cl⁻,
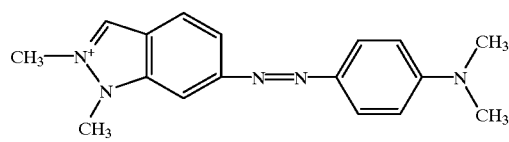 (I34) Cl⁻,
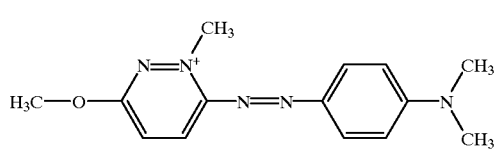 (I35) Cl⁻,
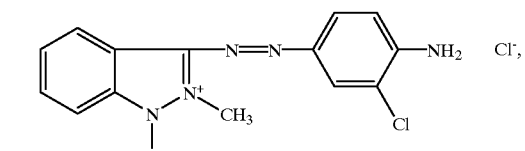 (I36) Cl⁻,
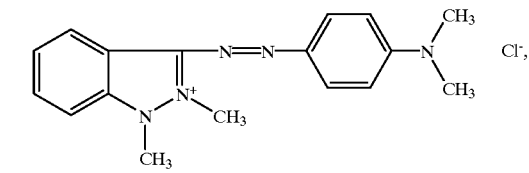 (I37) Cl⁻,
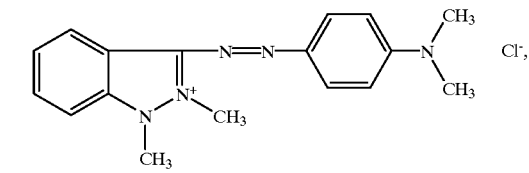 (I38) Cl⁻,
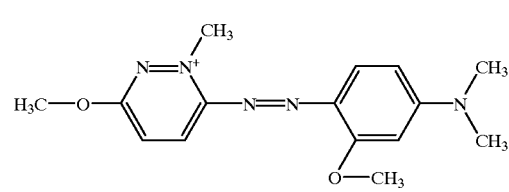 (I39) Cl⁻,
-continued
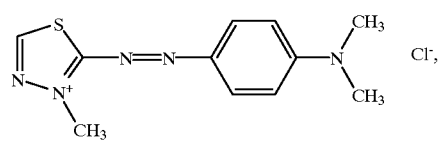 (I40) Cl⁻,
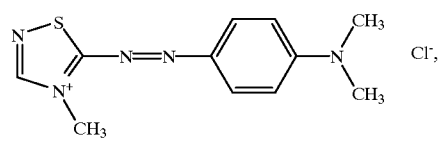 (I41) Cl⁻,
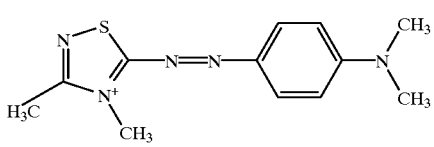 (I42) Cl⁻,
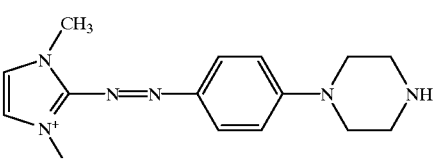 (I43) Cl⁻,
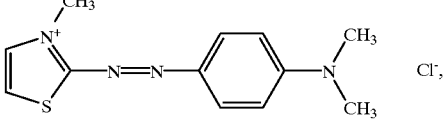 (I44) Cl⁻,
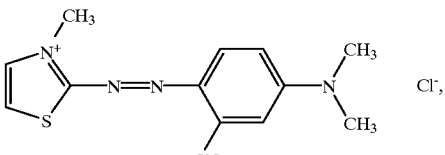 (I45) Cl⁻,
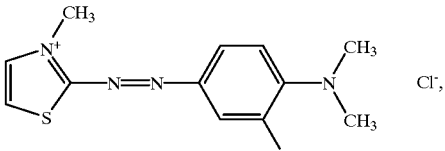 (I46) Cl⁻,
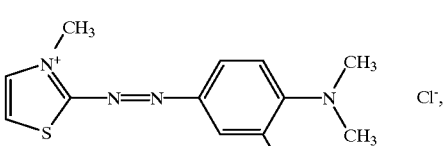 (I47) Cl⁻,
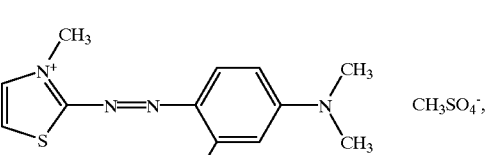 (I48) CH₃SO₄⁻,

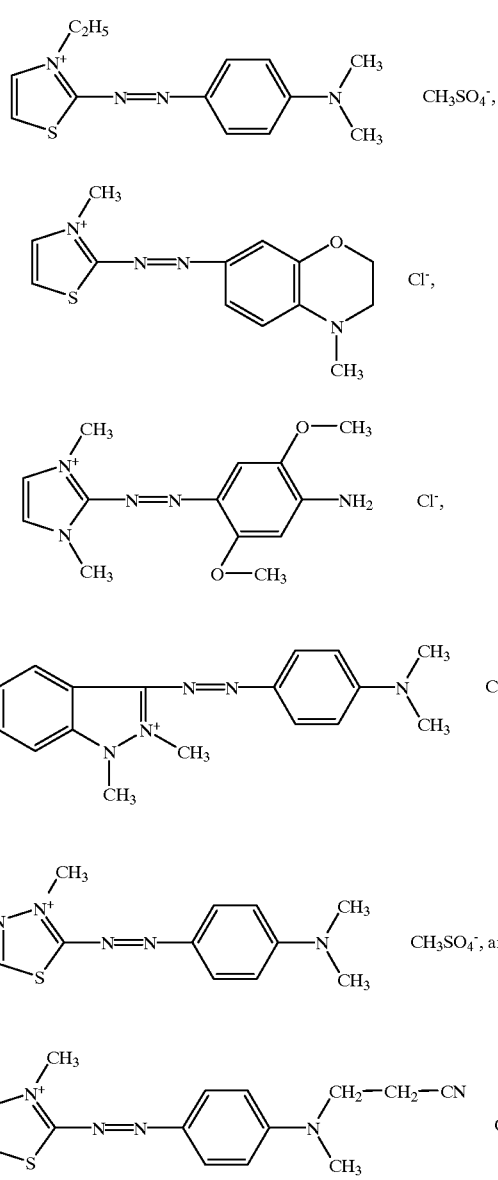

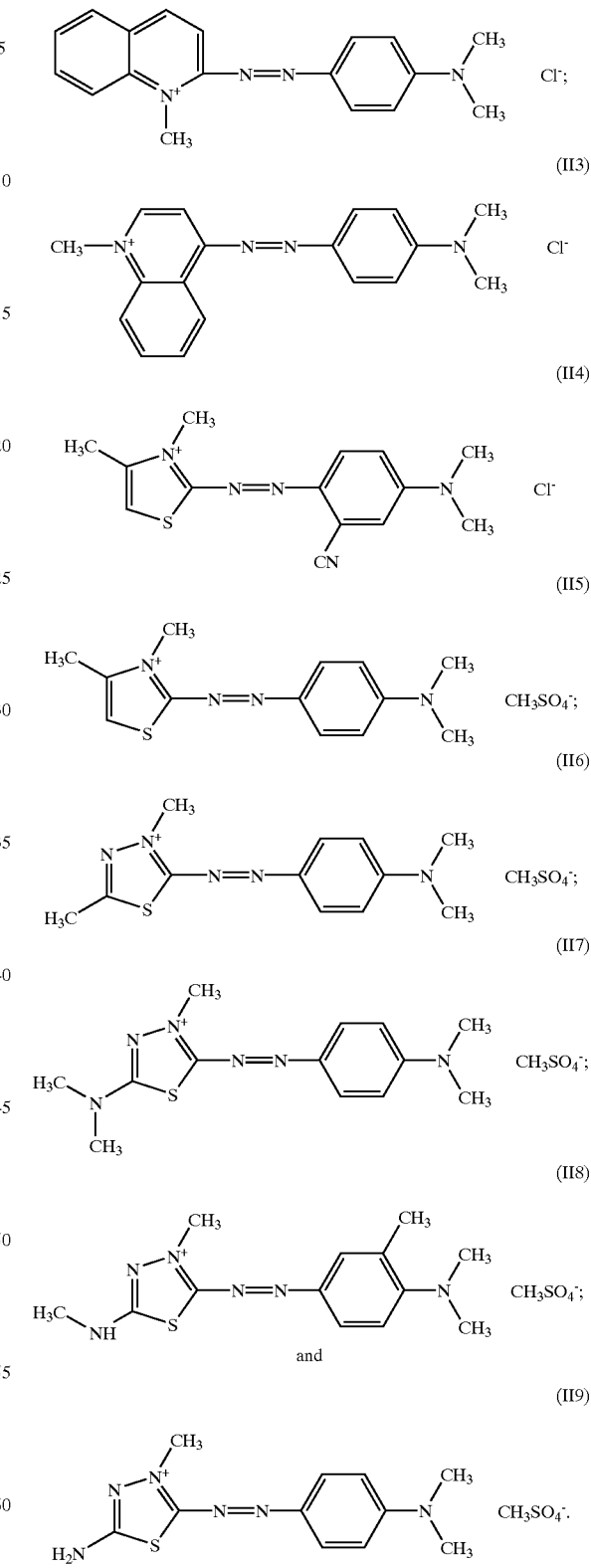

Among the compounds of structures (I1) to (I52) described above, the compounds most particularly preferred are those corresponding to structures (I1), (I2), (I14) and (I31).

Among the cationic direct dyes of formula (II) which can be used in the dye compositions in accordance with the invention, mention may be made more particularly of the compounds corresponding to structures (II1) to (II9) below:

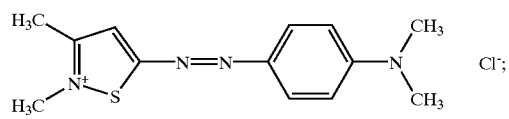

Among the cationic direct dyes of formula (III) which can be used in the dye compositions in accordance with the invention, mention may be made more particularly of the compounds corresponding to structures (III1) to (III18) below:
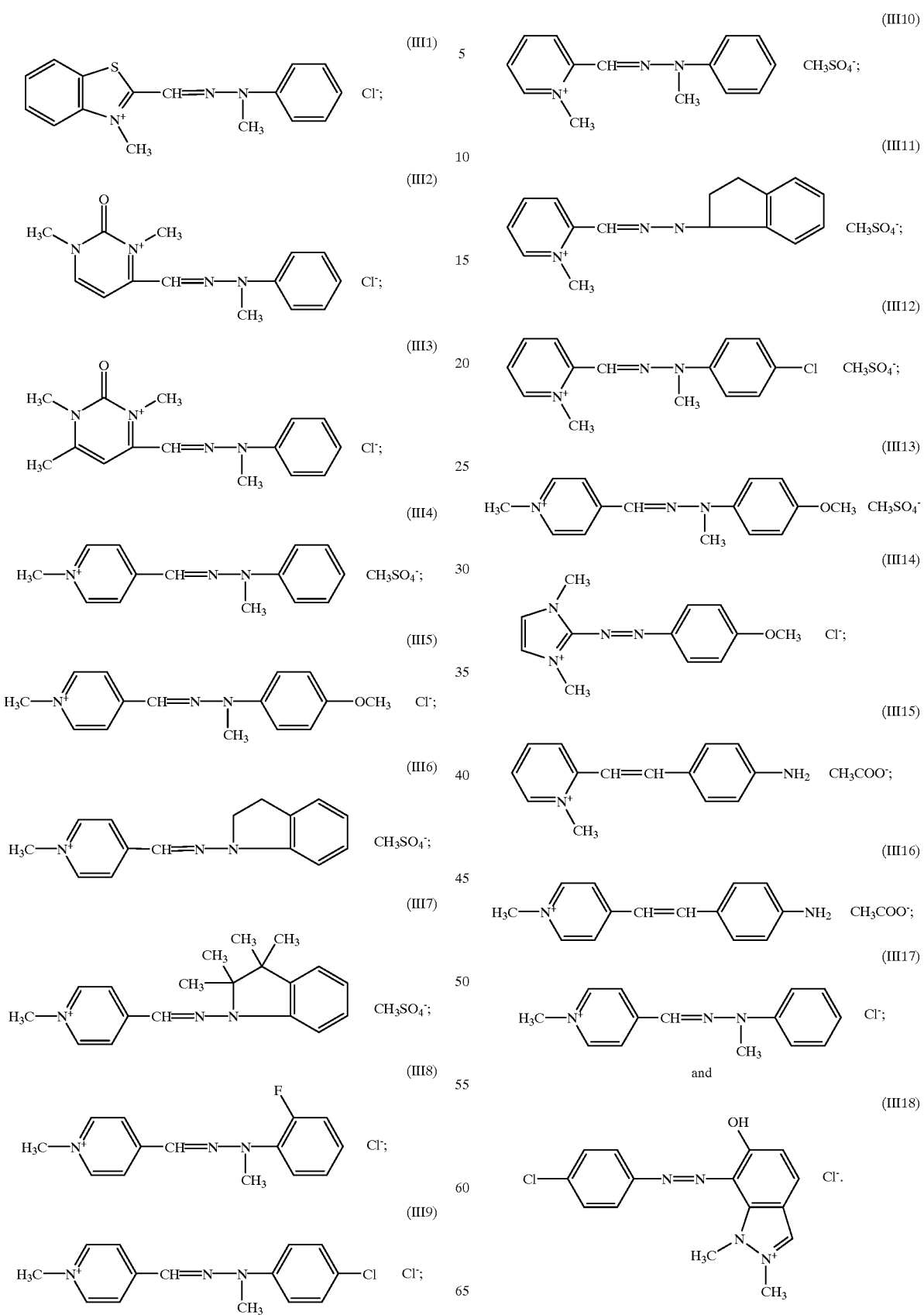

Among the specific compounds of structures (III1) to (III18) described above, the compounds most particularly preferred are those corresponding to structures (III4), (III5) and (III13).

Among the cationic direct dyes of formula (III') which can be used in the dye compositions in accordance with the invention, mention may be made more particularly of the compounds corresponding to structures (III'1) to (III'3) below:

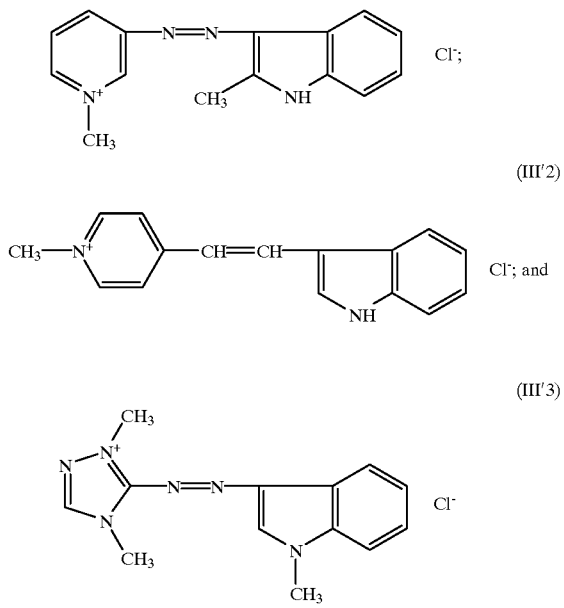

The cationic direct dye(s) used according to the invention preferably represent(s) from 0.001 to 10% by weight approximately relative to the total weight of the dye composition, and even more preferably from 0.005 to 5% by weight approximately relative to this weight.

(ii) For the purposes of the invention, the term "polyol" denotes a compound of linear, branched or cyclic, saturated or unsaturated alkyl type bearing at least two —OH functions on the alkyl chain, as well as the polymers (polyethers) of these polyhydroxyalkyl compounds.

The alkyl compound preferably contains from 2 to 12 carbon atoms and even more preferably from 2 to 9.

The polyols used according to the invention can be chosen in particular from $C_2$–$C_9$ polyols, as well as polyalkylene glycols such as, more particularly, polyethylene glycols and polypropylene glycols.

Among the $C_2$–$C_9$ polyols, mention may be made in particular of glycerol, propylene glycol, 1,3-propanediol, 2-butene-1,4-diol, pentane-1,5-diol, 2,2-dimethylpropane-1,3-diol, 3-methylpentane-1,5-diol, pentane-1,2-diol, 2,2,4-trimethylpentane-1,3-diol, 2-methhylpropane-1,3-diol, hexylene glycol, 1,3-butylene glycol, dipropylene glycol, diethylene glycol and triethylene glycol.

The specific polyol ethers according to the invention are chosen from $C_1$–$C_8$ aliphatic ethers of $C_3$–$C_9$ polyols and $C_6$–$C_8$ aromatic ethers of $C_2$–$C_9$ polyols.

Among the $C_1$–$C_8$ aliphatic ethers of $C_3$–$C_9$ polyols, mention may be made in particular of propylene glycol monomethyl ether, propylene glycol monoethyl ether, isopropylene glycol dimethyl ether, diethylene glycol monomethyl ether, diethylene glycol monoethyl ether, dipropylene glycol monomethyl ether, tripropylene glycol monomethyl ether and diethylene glycol dimethyl ether.

Among the $C_6$–$C_8$ aromatic ethers of $C_2$–$C_9$ polyols, mention may be made in particular of ethylene glycol monophenyl ether, ethylene glycol monobenzyl ether, propylene glycol monophenyl ether, propylene glycol monobenzyl ether, diethylene glycol monophenyl ether and diethylene glycol monobenzyl ether.

The polyol(s) and/or the polyol ether(s) described for the purposes of the invention are present in the dye composition in accordance with the invention in proportions generally ranging from 0.1 to 40% by weight, and even more particularly from 0.5 to 20% by weight, relative to the total weight of the composition.

The medium which is suitable for dyeing (or support) generally comprises a mixture of water and at least one polyol and/or polyol ether as defined above. It can also contain one or more organic solvents other than the polyol(s) and/or polyol ether(s) used in accordance with the invention, in order to dissolve the compounds which would not be sufficiently soluble in the medium. Organic solvents which may be mentioned, for example, are $C_1$–$C_4$ alkanols, such as ethanol and isopropanol, as well as aromatic alcohols such as benzyl alcohol, similar products and mixtures thereof.

The said additional organic solvents can be present in proportions preferably ranging from 0.5 to 40% by weight approximately relative to the total weight of the dye composition, and even more preferably from 1 to 20% by weight approximately.

The pH of the dye composition in accordance with the invention generally ranges from 2 to 11 approximately, and preferably from 5 to 10 approximately. It can be adjusted to the desired value using acidifying or basifying agents usually used for the direct dyeing of keratin fibres.

Among the acidifying agents, mention may be made of, for example, inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made of, for example, aqueous ammonia, alkaline carbonates, alkanolamines such as mono-, di- and triethanolamines and derivatives thereof, sodium hydroxide, potassium hydroxide and the compounds of formula (IV) below:

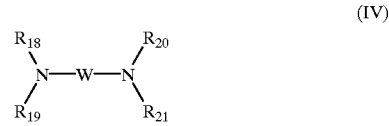

in which W is a propylene residue optionally having a substituent chosen from a hydroxyl group and $C_1$–$C_6$ alkyl radicals; $R_{18}$, $R_{19}$, $R_{20}$ and $R_{21}$, which may be identical or different, are chosen from a hydrogen atom and $C_1$–$C_6$ alkyl and $C_1$–$C_6$ hydroxylalkyl radicals.

In addition to the cationic direct dye(s) (i) defined above, the dye composition in accordance with the invention can contain one or more additional direct dyes which may be chosen, for example, from nitrobenzene dyes, anthraquinone dyes, naphthoquinone dyes, triarylmethane dyes, xanthene dyes and azo dyes which are non-cationic.

The dye composition in accordance with the invention can also contain various adjuvants conventionally used in compositions for the direct dyeing of the hair, such as antioxidants, penetrating agents, sequestering agents, fragrances, buffers, dispersing agents, surfactants, film-forming agents, ceramides, preserving agents, screening agents and opacifiers.

Needless to say, a person skilled in the art will take care to select this or these optional complementary compound(s) such that the advantageous properties intrinsically associated with the direct dye composition in accordance with the invention are not, or are not substantially, adversely affected by the addition(s) envisaged.

The direct dye composition according to the invention can be in various forms, such as in the form of liquids, shampoos, creams or gels or any other form which is suitable for dyeing keratin fibres, and in particular human hair. It can be obtained by mixing, at the time of use, a composition, which may be a in pulverulent form, containing the cationic direct dye(s) with a composition containing the specific polyol(s) and/or polyol ether(s).

When the combination of the cationic direct dye (i) and the polyol and/or polyol ether (ii) according to the invention is used in a composition intended for lightening direct dyeing, then the dye composition in accordance with the invention also contains at least one oxidizing agent other than an enzyme such as oxidases and oxidoreductases but chosen, for example, from hydrogen peroxide, urea peroxide, alkali metal bromates, persalts such as perborates and persulphates. The use of hydrogen peroxide is particularly preferred.

Another subject of the invention is a process for the direct dyeing of keratin fibres, and in particular human keratin fibres such as the hair, using the dye composition as defined above.

According to a first variant of this direct dyeing process in accordance with the invention, at least one dye composition as defined above is applied to the fibres, for a period which is sufficient to develop the desired coloration, after which the fibres are rinsed, optionally washed with shampoo, rinsed again and dried.

The time required to develop the coloration on the keratin fibres generally ranges from 3 to 60 minutes and even more precisely from 5 to 40 minutes.

According to a second variant of this direct dyeing process in accordance with the invention, at least one dye composition as defined above is applied to the fibres, for a period which is sufficient to develop the desired coloration, without final rinsing.

According to another specific embodiment of this direct dyeing process, and when the dye composition in accordance with the invention contains at least one oxidizing agent, the dyeing process includes a preliminary step which consists in separately storing, on the one hand, a composition (A) comprising, in a medium which is suitable for dyeing, at least one cationic direct dye as defined above and, on the other hand, a composition (B) containing, in a medium which is suitable for dyeing, at least one oxidizing agent, and then in mixing them together at the time of use, after which this mixture is applied to the keratin fibres, composition (A) or composition (B) containing at least one polyol and/or polyol ether as defined above.

Another subject of the invention is a multi-compartment dyeing device or "kit" or any other multi-compartment packaging system, a first compartment of which contains composition (A) as defined above and a second compartment of which contains composition (B) as defined above. These devices can be equipped with means for delivering the desired mixture onto the hair, such as the devices described in patent FR-2,586,913 in the name of L'Oréal, the disclosure of which is specifically incorporated by reference herein.

The examples which follow are intended to illustrate the invention without, however, limiting its scope.

EXAMPLES

Example 1

The dye composition below was prepared:

| Cationic direct dye of formula I(14) |       | 0.2 g |
|---|---|---|
| Propylene glycol |       | 10.0 g |
| 2-Amino-2-methylpropanol | qs pH 9 | |
| Demineralized water | qs | 100 g |

A.M.*: Active Material

The above composition was applied for 30 minutes to locks of natural grey hair containing 90% white hairs. The locks of hair were then rinsed, washed with a standard shampoo and then dried.

They were dyed an intense orange shade.

Example 2

The dye composition below was prepared:

| Cationic direct dye of formula I(1) |       | 0.2 g |
|---|---|---|
| Propylene glycol monomethyl ether |       | 10.0 g |
| 2-Amino-2-methylpropanol | qs pH 9 | |
| Demineralized water | qs | 100 g |

A.M.*: Active Material

The above composition was applied for 30 minutes to locks of natural grey hair containing 90% white hairs. The locks of hair were then rinsed, washed with a standard shampoo and then dried.

They were dyed an intense red shade.

What is claimed is:

1. A composition for the direct dyeing of keratin fibers comprising:

(i) at least one cationic direct dye chosen from those of formulae (I), (II), (III) and (III') below:

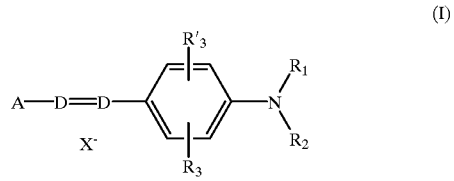

(I)

in which formula (I):

D is chosen from a nitrogen atom and a —CH group, $R_1$ and $R_2$, which may be identical or different, are chosen from a hydrogen atom, $C_1$–$C_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals, $R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, $X^-$ is an anion, A is a group chosen from structures $A_1$ to $A_{18}$ below:

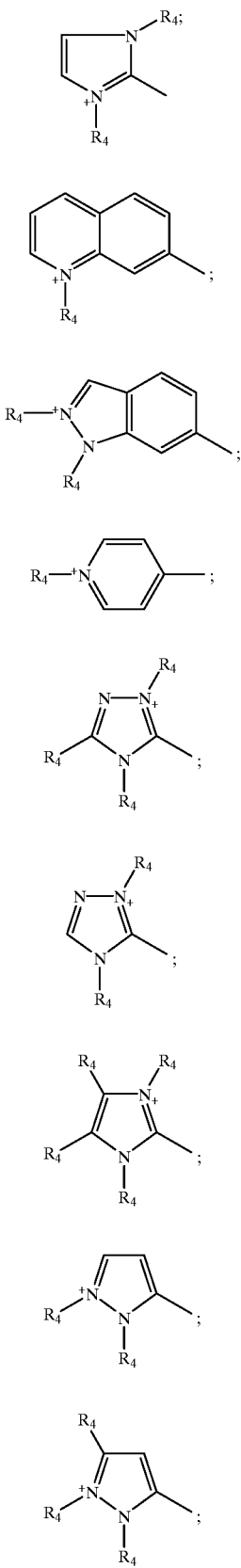

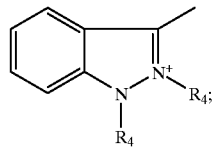

$A_{10}$

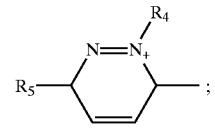

$A_{11}$

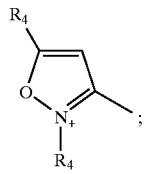

$A_{12}$

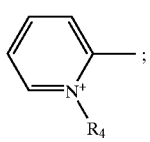

$A_{13}$

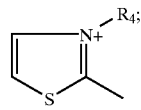

$A_{14}$

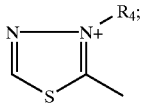

$A_{15}$

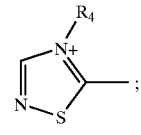

$A_{16}$

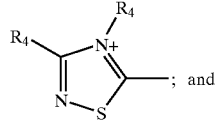

$A_{17}$; and

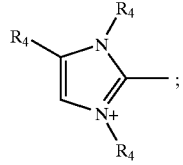

$A_{18}$ in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

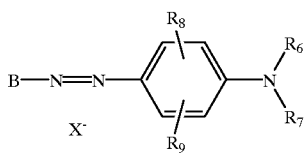
(II)

in which formula (II):

$R_6$ is chosen from a hydrogen atom and $C_1$–$C_4$ alkyl radicals, $R_7$ is chosen from a hydrogen atom, alkyl radicals having a substituent chosen from —CN and amino radicals, and a 4'-aminophenyl radical, or forms, with $R_6$, a nitrogenous heterocycle optionally oxygenated and optionally having a substituent chosen from $C_1$–$C_4$ alkyl radicals, $R_8$ and $R_9$, which may be identical or different, are chosen from a hydrogen atom, halogen atoms, and $C_1$–$C_4$ alkyl, $C_1$–$C_4$ alkoxy, and —CN radicals, $X^-$ is an anion, B is a group chosen from structures B1 to B6 below:

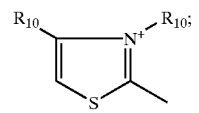 B1

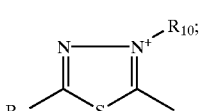 B2

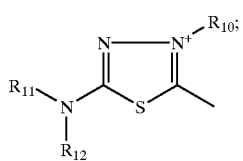 B3

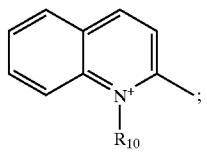 B4

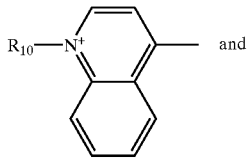 B5

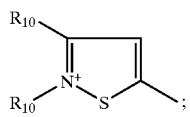 B6 in which $R_{10}$ is chosen from $C_1$–$C_4$ alkyl radicals, and $R_{11}$ and $R_{12}$, which may be identical or different, are chosen from a hydrogen atom and $C_1$–$C_4$ alkyl radicals;

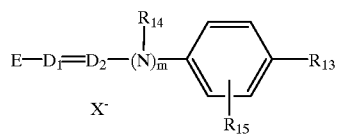 (III)

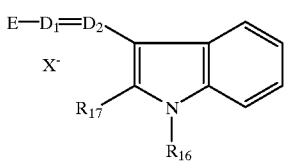 (III')

in which formulae (III) and (III'):

$R_{13}$ is chosen from a hydrogen atom, $C_1$–$C_4$ alkoxy radicals, halogen atoms chosen from bromine, chlorine, iodine and fluorine and unsubstituted and substituted amino radicals, $R_{14}$ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals, $R_{15}$ is chosen from a hydrogen atom and halogen atoms chosen from bromine, chlorine, iodine and fluorine, $R_{16}$ and $R_{17}$, which may be identical or different, are chosen from a hydrogen atom and $C_1$–$C_4$ alkyl radicals, $D_1$ and $D_2$, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

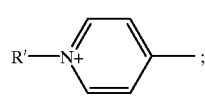 E1

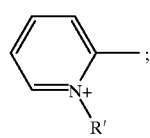 E2

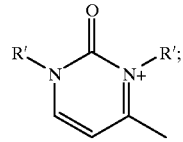 E3

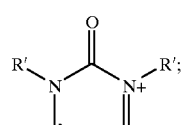 E4

-continued

E5
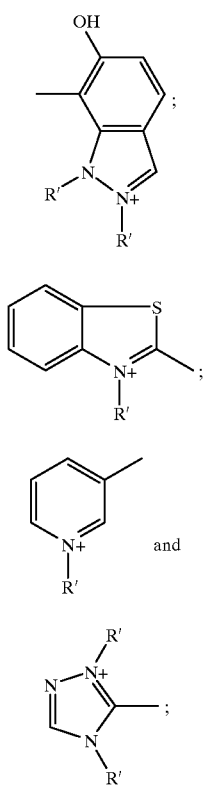

E6

E7
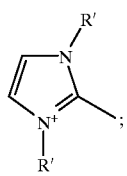 and

E8 in which R' is chosen from $C_1$–$C_4$ alkyl radicals;
when m is 0 and when $D_1$ is a nitrogen atom, then E can also be a group of structure E9 below:

E9 in which R' is chosen from $C_1$–$C_4$ alkyl radicals; and
(ii) at least one compound chosen from $C_6$–$C_8$ aromatic ethers of $C_2$–$C_9$ polyols,
said composition being free of oxidases or oxidoreductases,
and wherein said at least one cationic direct dye and said at least one compound are present in an amount effective to acieve direct dyeing of said keratin fibers.

2. The composition according to claim 1, wherein X is chosen from chloride, methyl sulphate and acetate and wherein for $R_8$ and $R_9$, said halogen atoms are chosen from bromine, chlorine, iodine, and fluorine.

3. The composition according to claim 1, wherein said keratin fibers are human keratin fibers.

4. The composition according to claim 3, where said human keratin fibers are hair.

5. The composition according to claim 1, wherein said at least one cationic direct dye of formula (I) is chosen from structures (I1) to (I54) below:

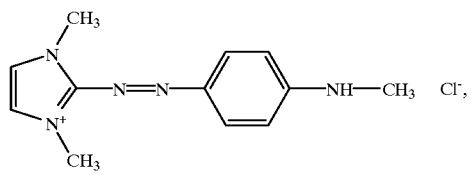
(I1)

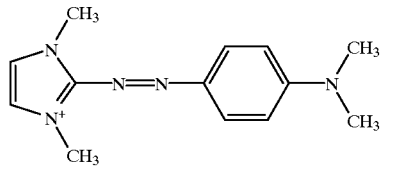
(I2)

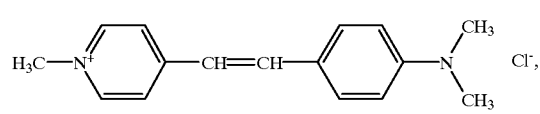
(I3)

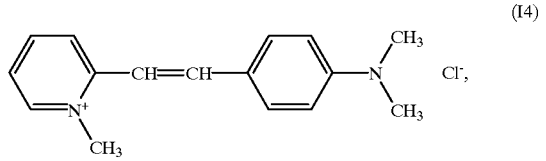
(I4)

(I5)

(I6)

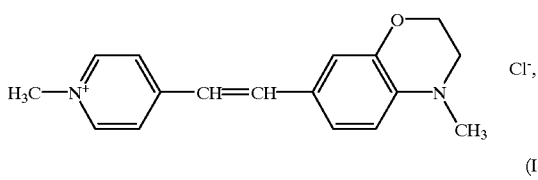
(I7)

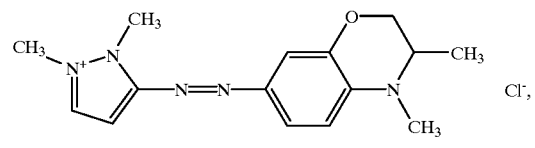
(I8)

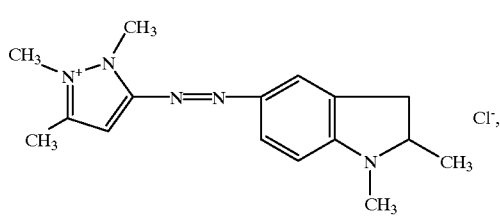
(I9)

(I10) 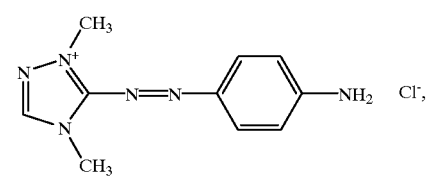 Cl⁻,
(I11) 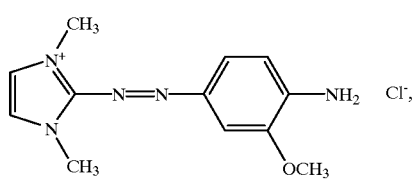 Cl⁻,
(I12) 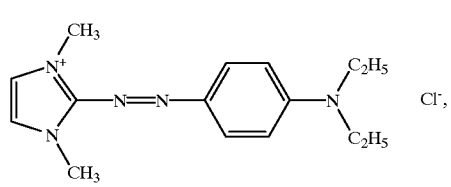 Cl⁻,
(I13) 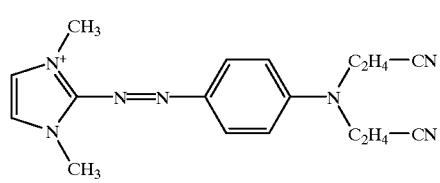 Cl⁻,
(I14) 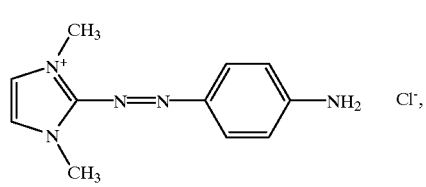 Cl⁻,
(I15) 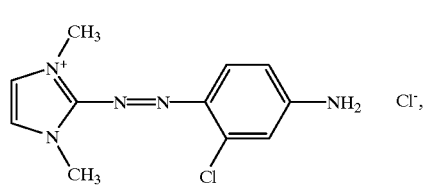 Cl⁻,
(I16) 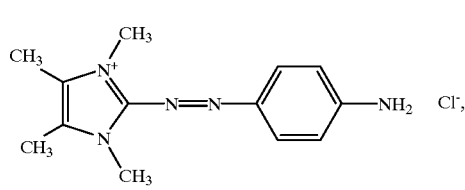 Cl⁻,
(I17) 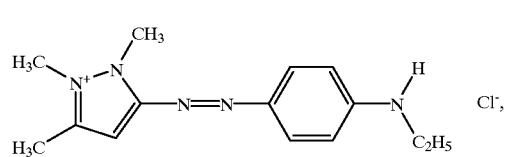 Cl⁻,
(I18) 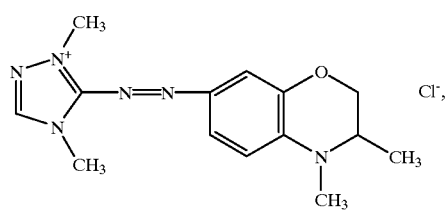 Cl⁻,
(I19) 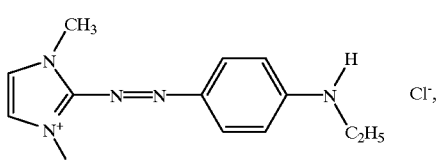 Cl⁻,
(I20) 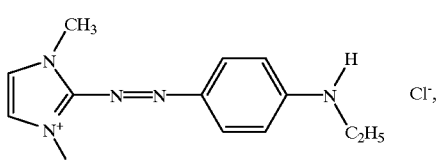 Cl⁻,
(I21) 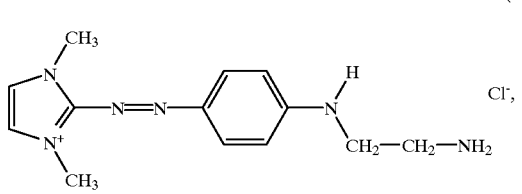 Cl⁻,
(I22) 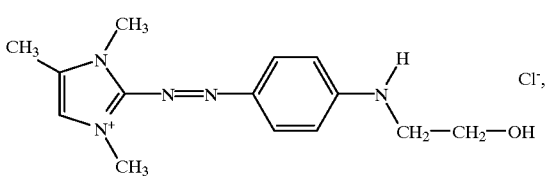 Cl⁻,
(I23) 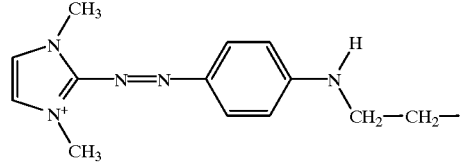 Cl⁻,
(I24) 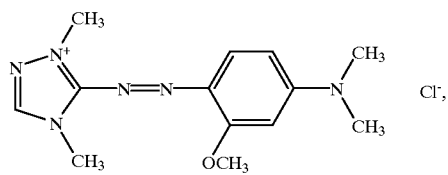 Cl⁻,
(I25) 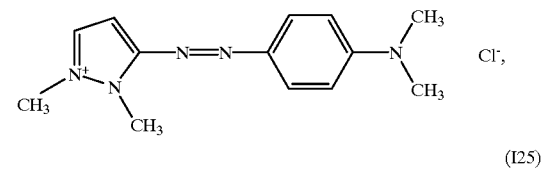 Cl⁻,

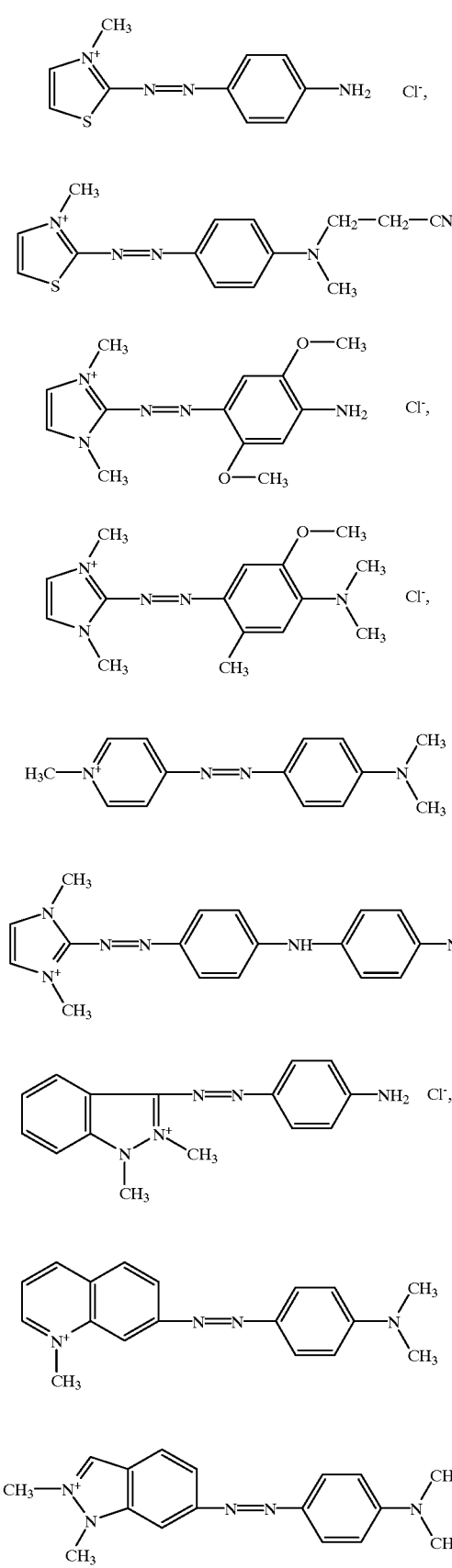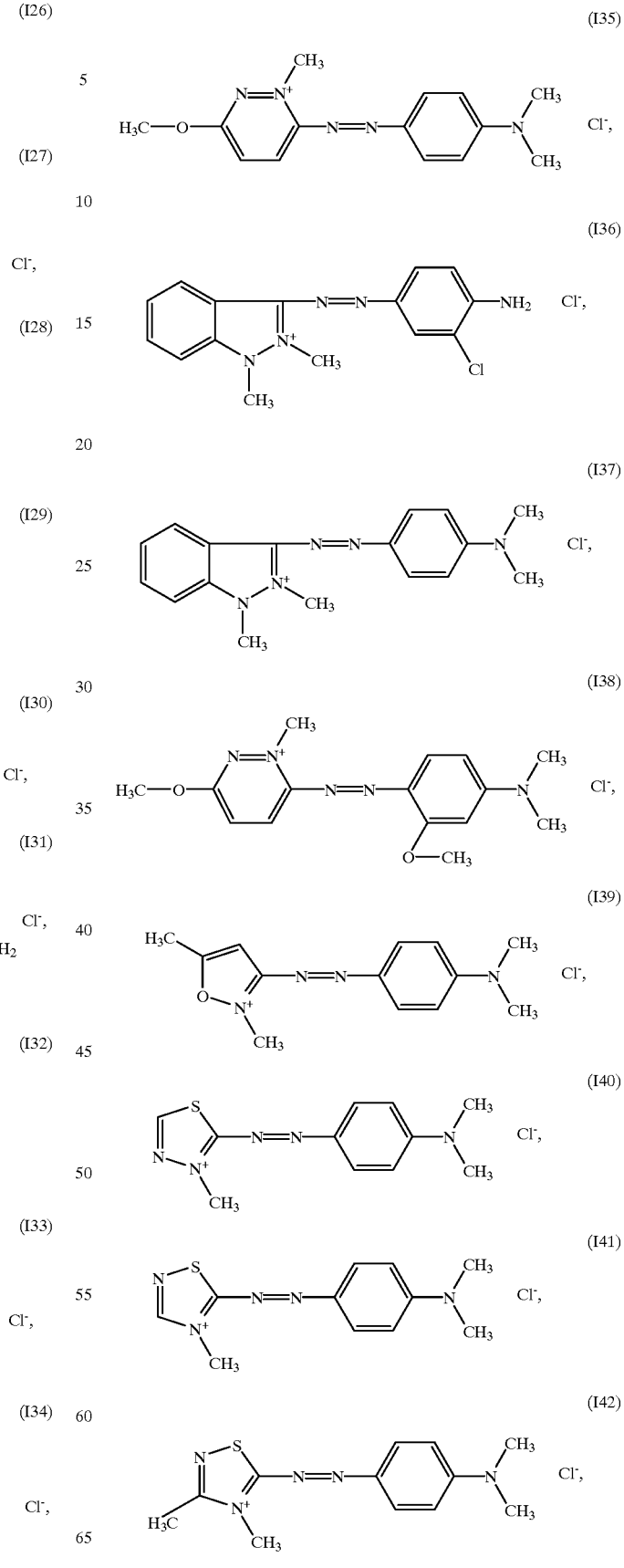

(I43)
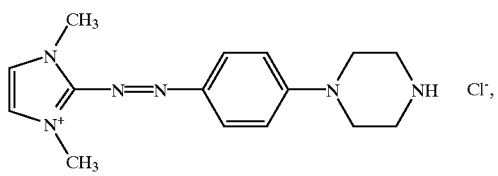
Cl⁻,
(I44)
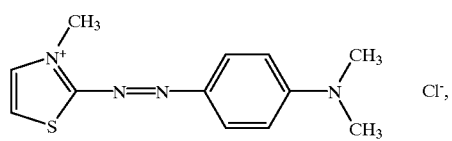
Cl⁻,
(I45)
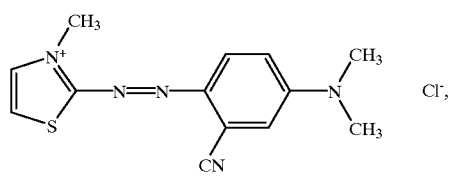
Cl⁻,
(I46)
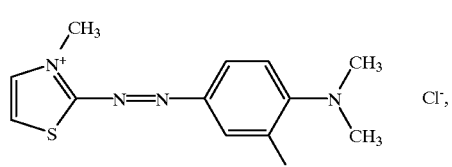
Cl⁻,
(I47)
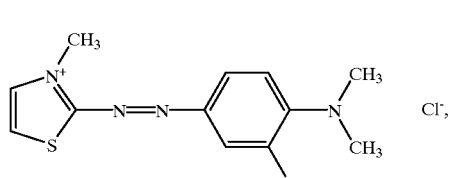
Cl⁻,
(I48)
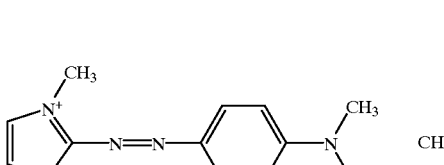
CH₃SO₄⁻,
(I49)
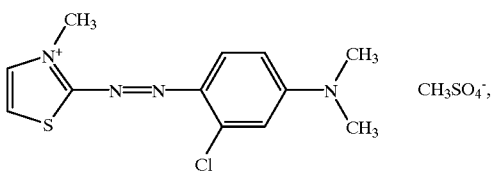
CH₃SO₄⁻,
(I50)
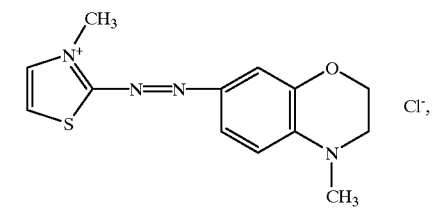
Cl⁻,
(I51)
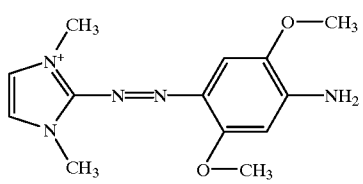
Cl⁻,
(I52)
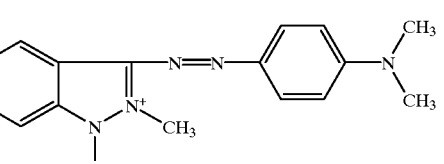
Cl⁻,
(I53)
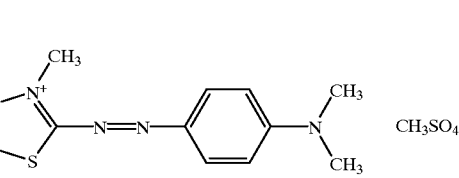
CH₃SO₄⁻, and
(I54)
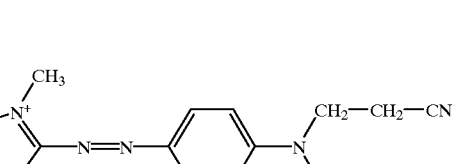
Cl⁻.
6. The composition according to claim 5, wherein said at least one cationic direct dye is chosen from structures (I1), (I2), (I14) and (I31).
7. The composition according to claim 1, wherein said at least one cationic direct dye of formula (II) is chosen from structures (II1) to (II9) below:
(II1)
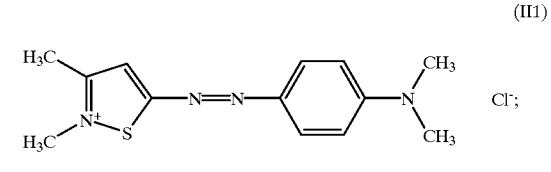
Cl⁻;
(II2)
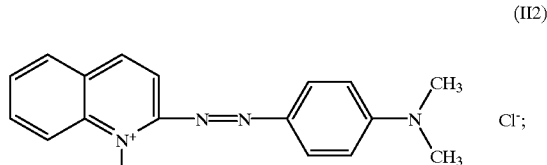
Cl⁻;
(II3)
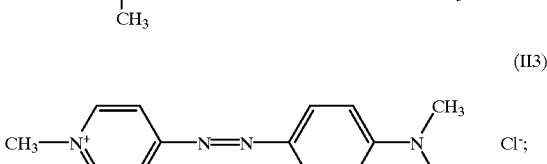
Cl⁻;

(II4)
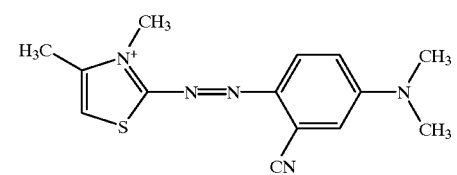
(II5)
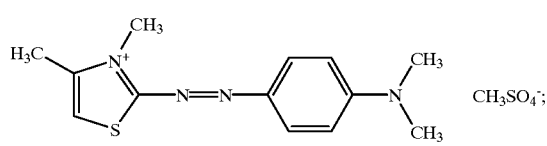
(II6)
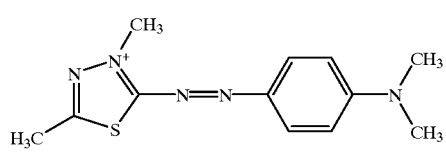
(II7)
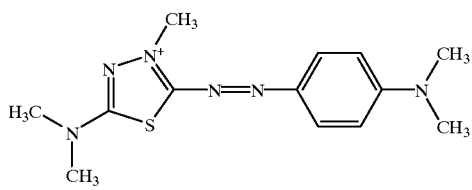
(II8)
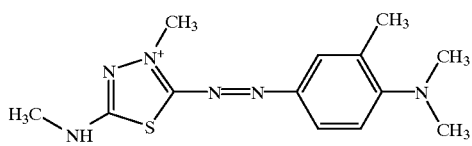
and
(II9)
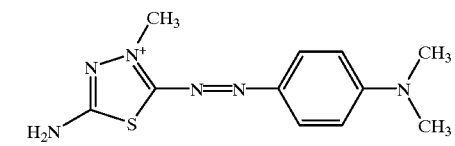
8. The composition according to claim 1, wherein said at least one cationic direct dye of formula (III) is chosen from structures (III1) to (III18) below:
(III1)
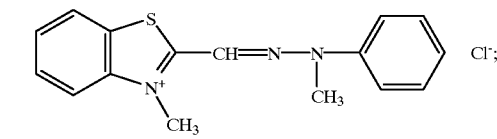
(III2)
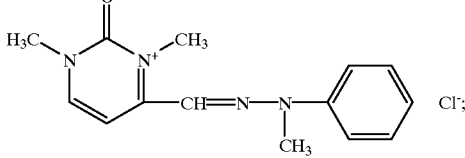
(III3)
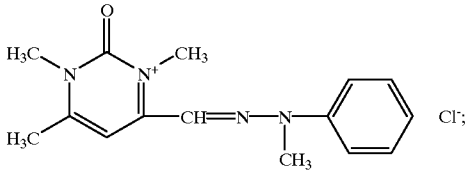
(III4)
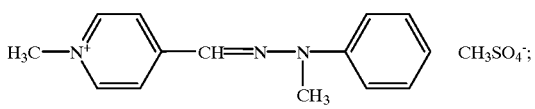
(III5)
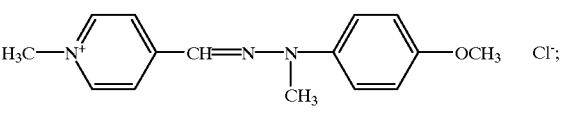
(III6)
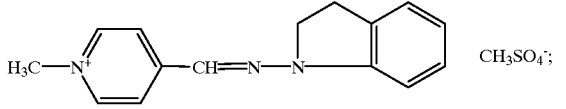
(III7)
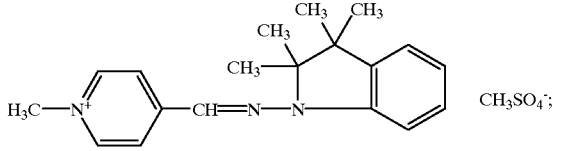
(III8)
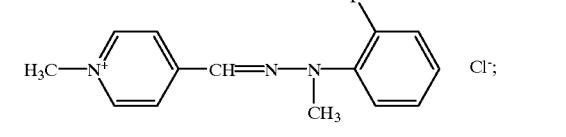
(III9)
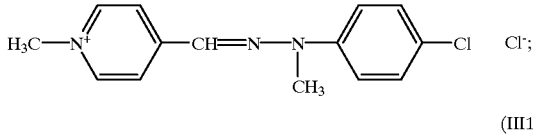
(III10)
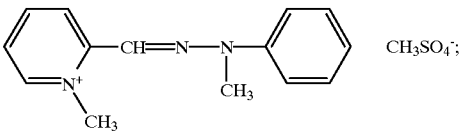

-continued (III11) [structure with pyridinium-CH=N-N-indanyl, CH₃SO₄⁻]

(III12) [pyridinium-CH=N-N(CH₃)-phenyl-Cl, CH₃SO₄⁻]

(III13) H₃C-pyridinium-CH=N-N(CH₃)-phenyl-OCH₃, CH₃SO₄⁻

(III14) [imidazolium-N=N-phenyl-OCH₃, Cl⁻]

(III15) [pyridinium-CH=CH-phenyl-NH₂, CH₃COO⁻]

(III16) H₃C-pyridinium-CH=CH-phenyl-NH₂, CH₃COO⁻

(III17) H₃C-pyridinium-CH=N-N(CH₃)-phenyl, Cl⁻ and (III18) [Cl-phenyl-N=N-indazolium with OH, N-CH₃, N⁺-CH₃], Cl⁻

9. The composition according to claim 8, wherein said at least one cationic direct dye of formula (III) is chosen from structures (III4), (III5) and (III13).

10. The composition according to claim 1, wherein said at least one cationic direct dye of formula (III') is chosen from structures (III'1) to (III'3) below:

(III'1) [pyridinium-N=N-indolyl(CH₃)(NH), Cl⁻]

(III'2) [CH₃-pyridinium-CH=CH-indolyl(NH), Cl⁻; and]

(III'3) [triazolium(CH₃)(CH₃)-N=N-indolyl(N-CH₃), Cl⁻]

11. The composition according to claim 1, wherein said $C_6$–$C_8$ aromatic ethers of $C_2$–$C_9$ polyols are chosen from ethylene glycol monophenyl ether, ethylene glycol monobenzyl ether, propylene glycol monophenyl ether, propylene glycol monobenzyl ether, diethylene glycol monophenyl ether and diethylene glycol monobenzyl ether.

12. The composition according to claim 1, wherein said at least one cationic direct dye is present in an amount ranging from 0.001 to 10% by weight relative to the total weight of the composition.

13. The composition according to claim 12, wherein said at least one cationic direct dye is present in an amount ranging from 0.005 to 5% by weight relative to the total weight of the composition.

14. The composition according to claim 1m wherein said at least one compound is present in an amount ranging from 0.1 to 40% by weight relative to the total weight of the composition.

15. The composition according to claim 14, wherein said at least one compound is present in an amount ranging from 0.5 to 20% by weight relative to the total weight of the composition.

16. The composition according to claim 1, wherein said composition further comprises additional direct dyes.

17. The composition according to claim 1, wherein said composition further comprises water.

18. The composition according to claim 17, wherein composition further comprises at least one organic solvent other than polyols, $C_1$–$C_8$ aliphatic ethers of $C_3$–$C_9$ polyols, and $C_6$–$C_8$ aromatic ethers of $C_2$–$C_9$ polyols.

19. The composition according claim 1, wherein said composition has a pH ranging from 2 to 11.

20. The composition according to claim 19, wherein said pH ranges from 5 to 10.

21. The composition according to claim 1, wherein said composition further comprises at least one oxidizing agent.

22. The composition according to claim 1, wherein said composition further comprises at least one oxidizing agent.

23. A process for the direct dyeing of keratin fibers, comprising applying to said fibersm for a period which is sufficient to develop a desired coloration, at least one composition for the first dyeing of keratin fibers comprising
   (i) at least one cationic direct dye chosen from those of formulae (I), (II), (III) and (III') below:

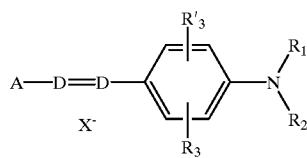 (I)

in which formula (I):

D is chosen from a nitrogen atom and a —CH group, $R_1$ and $R_2$, which may be identical or different, are chosen from a hydrogen atom, $C_1$–$C_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals, $R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, X$^-$ is an anion, A is a group chosen from structures $A_1$ to $A_{18}$ below:

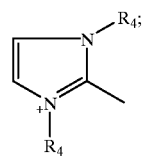 $A_1$

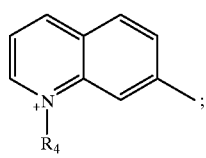 $A_2$

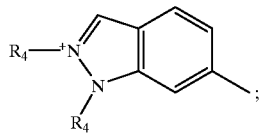 $A_3$

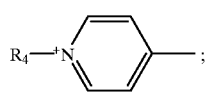 $A_4$

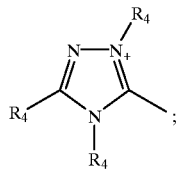 $A_5$

-continued

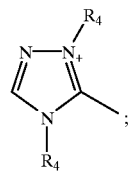 $A_6$

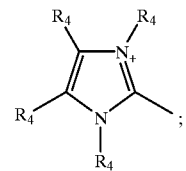 $A_7$

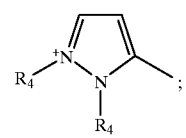 $A_8$

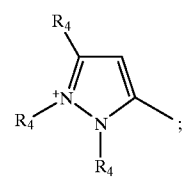 $A_9$

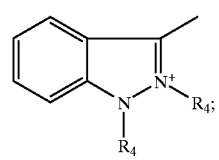 $A_{10}$

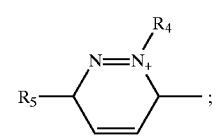 $A_{11}$

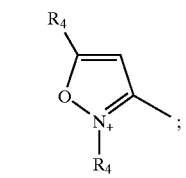 $A_{12}$

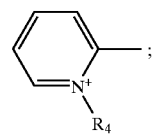 $A_{13}$

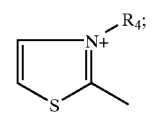 $A_{14}$

-continued

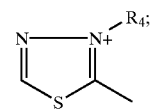
A15

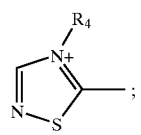
A16

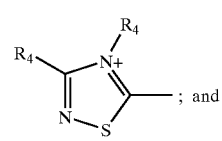
A17 ; and

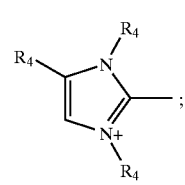
A18 in which R$_4$ is chosen from C$_1$–C$_4$ alkyl radicals which can be substituted with a hydroxyl radical and R$_5$ is chosen from C$_1$–C$_4$ alkoxy radicals, with the proviso that when D is —CH, when A is A$_4$ or A$_{13}$ and when R$_3$ is other than an alkoxy radical, then R$_1$ and R$_2$ are not simultaneously a hydrogen atom;

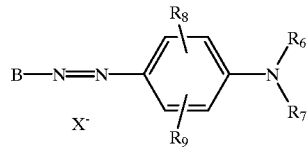
(II)

in which formula (II):

R$_6$ is chosen from a hydrogen atom and C$_1$–C$_4$ alkyl radicals,

R$_7$ is chosen from a hydrogen atom, alkyl radicals having a substituent chosen from —CN and amino radicals, and a 4'-aminophenyl radical, or forms, with R$_6$, a nitrogenous heterocycle optionally oxygenated and optionally having a substituent chosen from C$_1$–C$_4$ alkyl radicals, R$_8$ and R$_9$, which may be identical or different, are chosen from a hydrogen atom, halogen atoms, and C$_1$–C$_4$ alkyl, C$_1$–C$_4$ alkoxy, and —CN radicals, X$^-$ is an anion, B is a group chosen from structures B1 to B6 below:

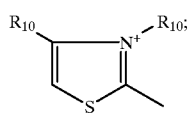
B1

-continued

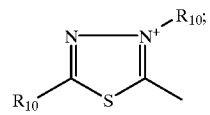
B2

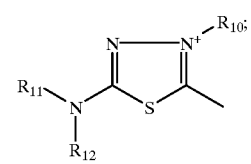
B3

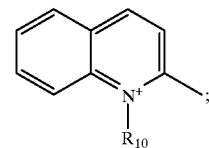
B4

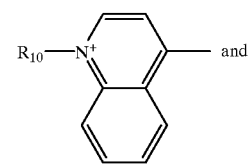
B5 and

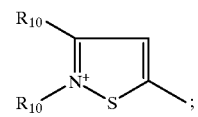
B6 in which R$_{10}$ is chosen from C$_1$–C$_4$ alkyl radicals, and R$_{11}$ and R$_{12}$, which may be identical or different, are chosen from a hydrogen atom and C$_1$–C$_4$ alkyl radicals;

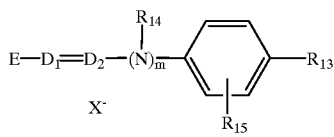
(III)

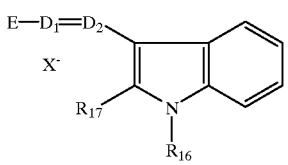
(III')

in which formulae (III) and (III'):

R$_{13}$ is chosen from a hydrogen atom, C$_1$–C$_4$ alkoxy radicals, halogen atoms chosen from bromine, chlorine, iodine and fluorine and unsubstituted and substituted amino radicals, R$_{14}$ is chosen from a hydrogen atom, and C$_1$–C$_4$ alkyl radicals or forms, with a carbon atom of the benzene ring, a heterocycle which is optionally oxygenated and optionally has a substituent chosen from C$_1$–C$_4$ alkyl radicals, R$_{15}$ is chosen from a hydrogen atom and halogen atoms chosen from bromine, chlorine, iodine and fluorine, R$_{16}$ and R$_{17}$, which may be identical or different, are chosen from a hydrogen atom and C$_1$–C$_4$ alkyl radicals, $D_1$ and $D_2$, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

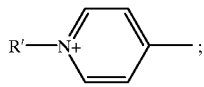
E1

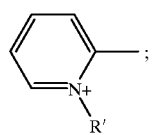
E2

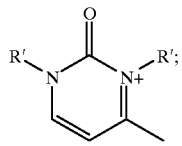
E3

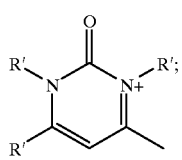
E4

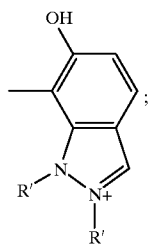
E5

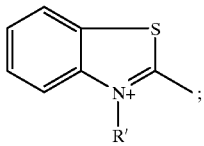
E6

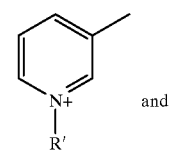
E7 and

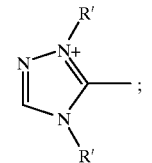
E8 in which R' is chosen from $C_1-C_4$ alkyl radicals;

when m is 0 and when $D_1$ is a nitrogen atom, then E can also be a group of structure E9 below:

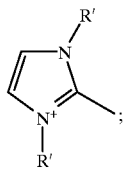
E9 in which R' is chosen from $C_1-C_4$ alkyl radicals;

(ii) at least one compound chosen from $C_6-C_8$ aromatic ethers of $C_2-C_9$ polyols, said composition being free of oxidases or oxidoreductases, and wherin said at least one cationic dye and said at least one compound are present in an amount effective to achieve direct dyeing of said keratin fibers;

rinsing the fibers, optionally washing said fibers with shampoo, then optionally rinsing again and drying.

24. A process for dyeing keratin fibers according to claim 23, wherein said keratin fibers are human keratin fibers.

25. A process for dyeing keratin fibers according to claim 24, wherein said human keratin fibers are hair.

26. A process for the direct dyeing of keratin fibers according to claim 23, wherein said fibers are not rinsed a second time before drying.

27. A process for the direct dyeing of keratin fibers comprising:

separately storing a first composition comprising:

(i) at least one cationic direct dye chosen from those of formulae (I), (II), (III) and (III') below:

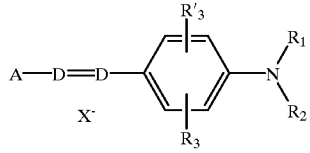
(I)

in which formula (I):

D is chosen from a nitrogen atom and a —CH group, $R_1$ and $R_2$, which may be identical or different, are chosen from a hydrogen atom, $C_1-C_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1-C_4$ alkyl radicals, $R_3$ and $R'_3$, which may be identical or different, are chosen from a hydrogen atom, halogen atoms chosen from chlorine, bromine, iodine and fluorine, and cyano, $C_1-C_4$ alkoxy, $C_1-C_4$ alkyl, and acetyloxy radicals, $X^-$ is an anion, A is a group chosen from structures $A_1$ to $A_{18}$ below:
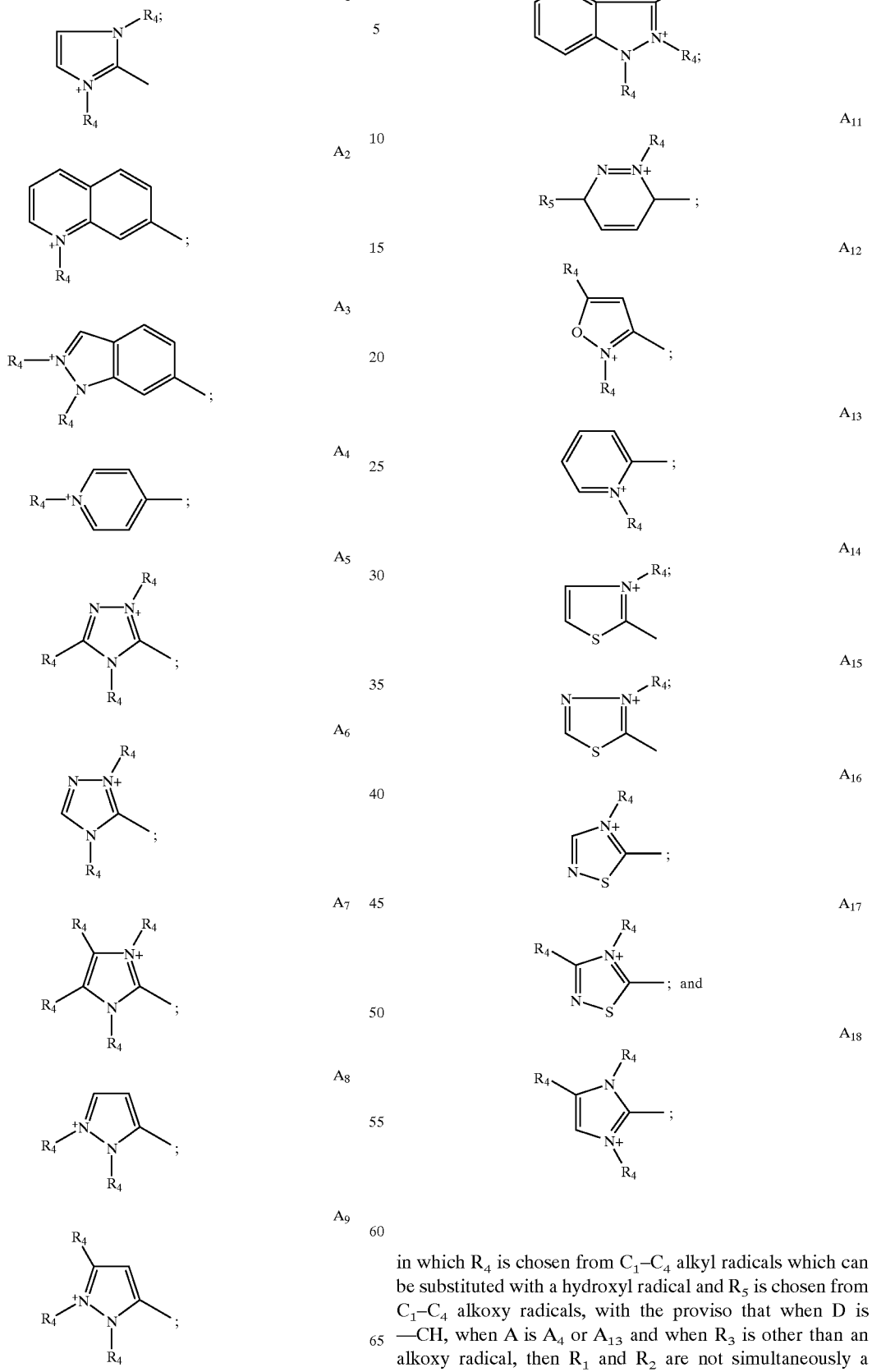
in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

(II)

[Structure II: B—N=N—pyridine ring with R8, R9 substituents and N(R6)(R7) group, X⁻ counterion]

in which formula (II):

R₆ is chosen from a hydrogen atom and $C_1$–$C_4$ alkyl radicals,

R₇ is chosen from a hydrogen atom, alkyl radicals having a substituent chosen from —CN and amino radicals, and a 4'-aminophenyl radical, or forms, with R₆, a nitrogenous heterocycle optionally oxygenated and optionally having a substituent chosen from $C_1$–$C_4$ alkyl radicals, R₈ and R₉, which may be identical or different, are chosen from a hydrogen atom, halogen atoms, and $C_1$–$C_4$ alkyl, $C_1$–$C_4$ alkoxy, and —CN radicals, X⁻ is an anion, B is a group chosen from structures B1 to B6 below:

B1
[thiazolium structure with R₁₀ substituents]

B2
[thiadiazolium structure with R₁₀ substituents]

B3
[thiadiazolium with NR₁₁R₁₂ substituent and R₁₀]

B4
[2-methylquinolinium with R₁₀ on N]

B5
[4-methylquinolinium with R₁₀ on N]

and

B6
[isothiazolium structure with R₁₀ substituents]

in which R₁₀ is chosen from $C_1$–$C_4$ alkyl radicals, and R₁₁ and R₁₂, which may be identical or different, are chosen from a hydrogen atom and $C_1$–$C_4$ alkyl radicals;

(III)

[Structure III: E—D₁=D₂—(N)ₘ—phenyl ring with R₁₃, R₁₄, R₁₅ substituents, X⁻ counterion]

(III')

[Structure III': E—D₁=D₂—indole ring with R₁₆, R₁₇ substituents, X⁻ counterion]

in which formulae (III) and (III'):

R₁₃ is chosen from a hydrogen atom, $C_1$–$C_4$ alkoxy radicals, halogen atoms chosen from bromine, chlorine, iodine and fluorine and unsubstituted and substituted amino radicals, R₁₄ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals, R₁₅ is chosen from a hydrogen atom and halogen atoms chosen from bromine, chlorine, iodine and fluorine, R₁₆ and R₁₇, which may be identical or different, are chosen from a hydrogen atom and $C_1$–$C_4$ alkyl radicals, D₁ and D₂, which may be identical or different, are chosen from a nitrogen atom and a —CH group, m is 0 or 1, it being understood that when R₁₃ is an unsubstituted amino radical, then D₁ and D₂ are simultaneously a —CH group and m is 0, X⁻ is an anion, E is a group chosen from structures E1 to E8 below:

E1
[4-pyridinium with R' on N]

E2
[2-pyridinium with R' on N]

E3
[pyrimidinone with R', R' substituents]

E4
[pyrimidinone with R', R', R' substituents]

-continued

E5

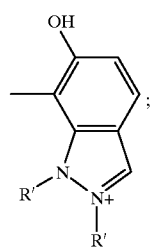

E6

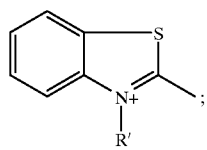

E7

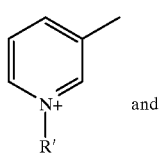 and

E8

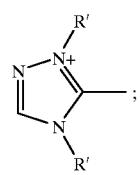

in which R' is chosen from C$_1$–C$_4$ alkyl radicals;

when m is 0 and when D$_1$ is a nitrogen atom, then E can also be a group of structure E9 below:

E9

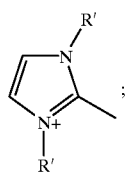

in which R' is chosen from C$_1$–C$_4$ alkyl radicals; and separately storing a second composition comprising at least one oxidizing agent other than oxidases or oxidoreductases and thereafter mixing said first composition with said second composition and applying this mixture to said keratin fibers, wherein said first and second composition additionally comprises at least one compound chosen from C$_6$–C$_8$ aromatic ethers of C$_2$–C$_9$ polyols, and wherein said at least one cationic direct dye and said at least one compound are present in an amount effective to achieve direct dyeing of said keratin fibers.

28. A composition for the direct dyeing of keratin fibers comprising:

(i) at least one cationic direct dye chosen from those of formulae (I), (II), (III) and (III') below:

(I)

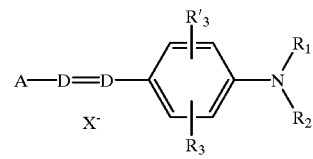

in which formula (I):

D is chosen from a nitrogen atom and a —CH group,

R$_1$ and R$_2$, which may be identical or different, are chosen from a hydrogen atom, C$_1$–C$_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from C$_1$–C$_4$ alkyl radicals, R$_3$ and R'$_3$, which may be identical or different, are chosen from a hydrogen atom, halogen atoms chosen from chlorine, bromine, iodine and fluorine, and cyano, C$_1$–C$_4$ alkoxy, C$_1$–C$_4$ alkyl, and acetyloxy radicals, X$^-$ is an anion, A is a group chosen from structures A$_1$ to A$_{18}$ below:

A$_1$

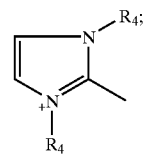

A$_2$

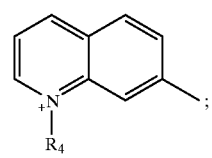

A$_3$

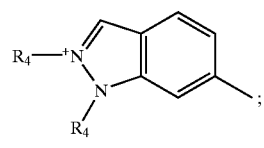

A$_4$

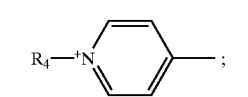

A$_5$

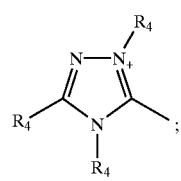

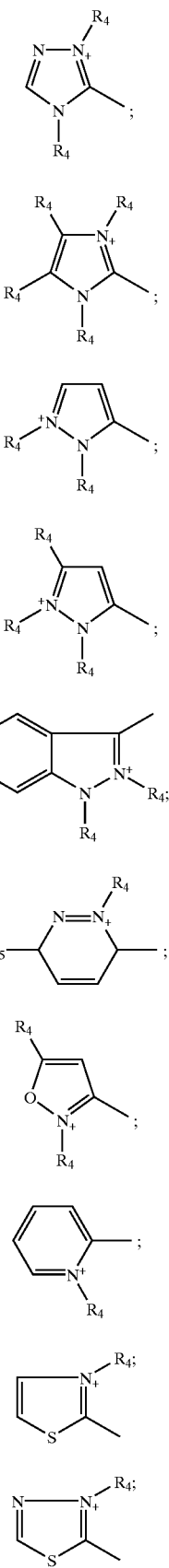

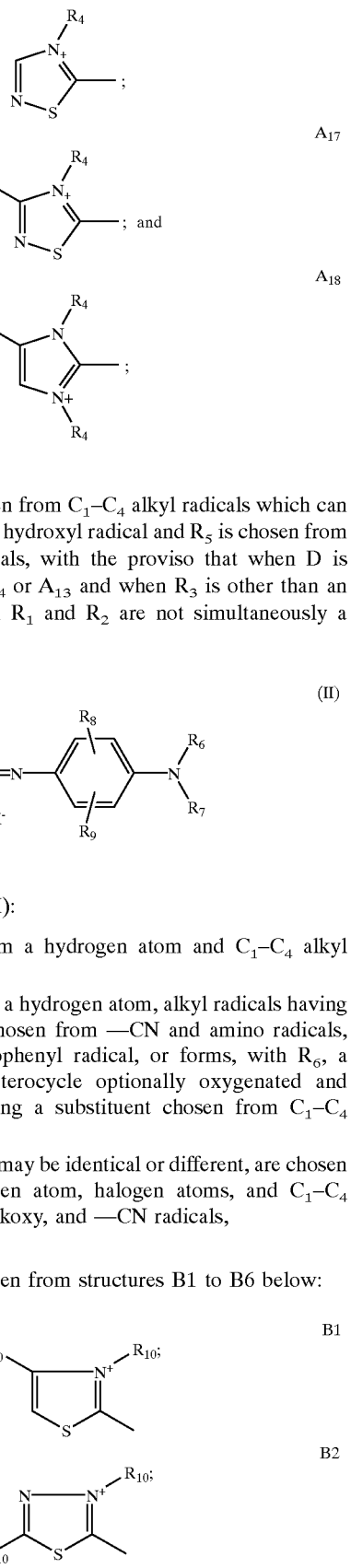

in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

(II)

in which formula (II):

$R_6$ is chosen from a hydrogen atom and $C_1$–$C_4$ alkyl radicals, $R_7$ is chosen from a hydrogen atom, alkyl radicals having a substituent chosen from —CN and amino radicals, and a 4'-aminophenyl radical, or forms, with $R_6$, a nitrogenous heterocycle optionally oxygenated and optionally having a substituent chosen from $C_1$–$C_4$ alkyl radicals, $R_8$ and $R_9$, which may be identical or different, are chosen from a hydrogen atom, halogen atoms, and $C_1$–$C_4$ alkyl, $C_1$–$C_4$ alkoxy, and —CN radicals, $X^-$ is an anion, B is a group chosen from structures B1 to B6 below:

-continued

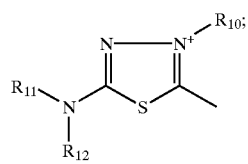
B3

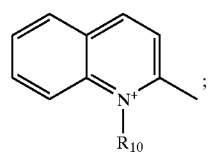
B4

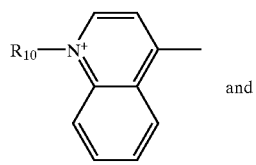
B5 and

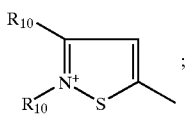
B6 in which $R_{10}$ is chosen from $C_1$–$C_4$ alkyl radicals, and $R_{11}$ and $R_{12}$, which may be identical or different, are chosen from a hydrogen atom and $C_1$–$C_4$ alkyl radicals;

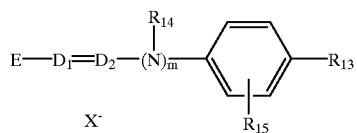
(III)

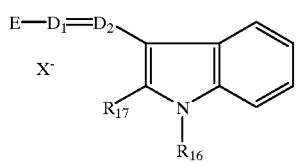
(III')

in which formulae (III) and (III'):

$R_{13}$ is chosen from a hydrogen atom, $C_1$–$C_4$ alkoxy radicals, halogen atoms chosen from bromine, chlorine, iodine and fluorine and unsubstituted and substituted amino radicals, $R_{14}$ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals, $R_{15}$ is chosen from a hydrogen atom and halogen atoms chosen from bromine, chlorine, iodine and fluorine, $R_{16}$ and $R_{17}$, which may be identical or different, are chosen from a hydrogen atom and $C_1$–$C_4$ alkyl radicals, $D_1$ and $D_2$, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

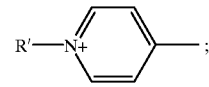
E1

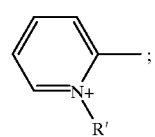
E2

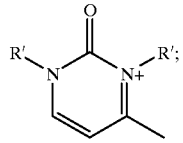
E3

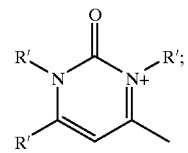
E4

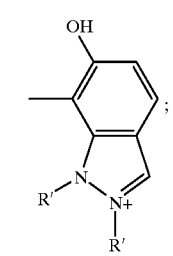
E5

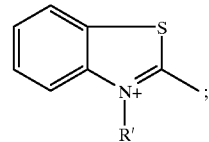
E6

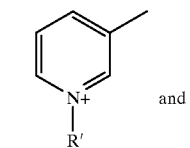
E7 and

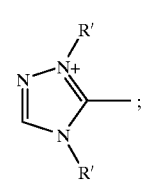
E8 in which R' is chosen from $C_1$–$C_4$ alkyl radicals;

when m is 0 and when $D_1$ is a nitrogen atom, then E can also be a group of structure E9 below:

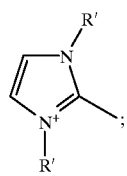

in which R' is chosen from $C_1$–$C_4$ alkyl radicals; and
(ii) at least one compound chosen from $C_6$–$C_8$ aromatic ethers of $C_2$–$C_9$ polyols,
said composition being free of oxidases or oxidoreductases,
and wherein said at least one cationic direct dye and said at least one compound are present in an amount effective to acieve direct dyeing of said keratin fibers.

29. The composition according to claim 28, wherein said $C_1$–$C_8$ aliphatic ethers of $C_3$–$C_9$ polyols are chosen from propylene glycol monomethyl ether, propylene glycol monoethyl ether, isopropylene glycol dimethyl ether, diethylene glycol monoethyl ether, diethylene glycol monoethyl ether, dipropylene glycol monomethyl ether, tripropylene glycol monomethyl ether and diethylene glycol dimethyl ether.

30. The composition according to claim 29, wherein said polyalkylene glycols are chosen from polyethylene glycols and polypropylene glycols.

31. The composition according to claim 29, wherein said $C_2$–$C_9$ polyols are chosen from glycerol, propylene glycol, 1,3-propanediol, 2-butene-1,4-diol, pentane-1,5-diol, 2,2-dimethylpropane-1,3-diol, 3-methylpentane-1,5-diol, pentane-1,2-diol, 2,2,4-trimethylpentane-1,3-diol, 2-methylpropane-1,3-diol, hexylene glycol, 1,3-butylene glycol, dipropylene glycol, diethylene glycol and triethylene glycol.

32. The composition according to claim 28, wherein said $C_1$–$C_8$ aliphatic ethers of $C_3$–$C_9$ polyols are chosen from propylene glycol monomethyl ether, propylene glycol monoethyl ether, isopropylene glycol dimethyl ether, diethylene glycol monoethyl ether, diethylene glycol monoethyl ether, dipropylene glycol monomethyl ether, triporopylene glycol monomethyl ether and diethylene glycol dimethyl ether.

33. A composition for the direct dyeing of keratin fibers comprising:
(i) at least one cationic direct dye chosen from those of formulae (I), (II), (III) and (III') below:

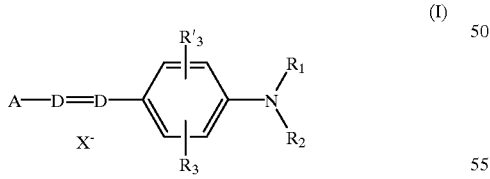

in which formula (I):
D is chosen from a nitrogen atom and a —CH group,
$R_1$ and $R_2$, which may be identical or different, are chosen from a hydrogen atom, $C_1$–$C_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals, $R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, $X^-$ is an anion, A is a group chosen from structures $A_2$, $A_3$, $A_5$, $A_6$, $A_{11}$, $A_{12}$, $A_{15}$, $A_{16}$ and $A_{17}$ below:

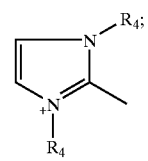

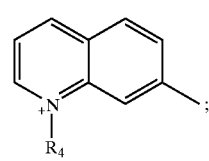

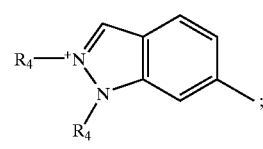

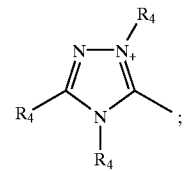

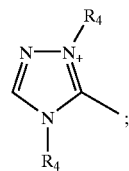

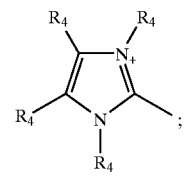

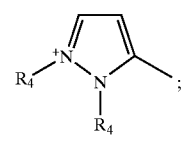

-continued

A₉ 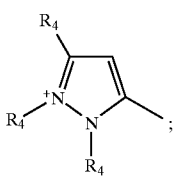

A₁₀ 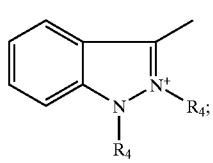

A₁₁ 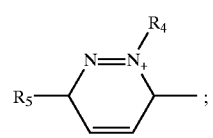

A₁₂ 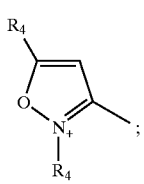

A₁₃ 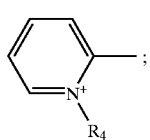

A₁₄ 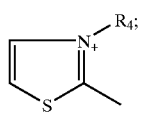

A₁₅ 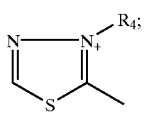

A₁₆ 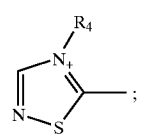

A₁₇ 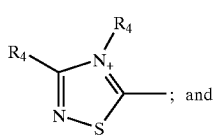; and

A₁₈ 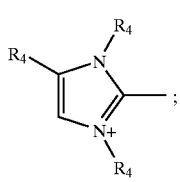

in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

(II)

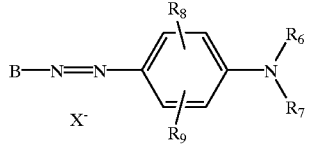

in which formula (II):

$R_6$ is chosen from a hydrogen atom and $C_1$–$C_4$ alkyl radicals, $R_7$ is chosen from a hydrogen atom, alkyl radicals having a substituent chosen from —CN and amino radicals, and a 4'-aminophenyl radical, or forms, with $R_6$, a nitrogenous heterocycle optionally oxygenated and optionally having a substituent chosen from $C_1$–$C_4$ alkyl radicals, $R_8$ and $R_9$, which may be identical or different, are chosen from a hydrogen atom, halogen atoms, and $C_1$–$C_4$ alkyl, $C_1$–$C_4$ alkoxy, and —CN radicals, $X^-$ is an anion, B is a group chosen from structures B2 and B3 below:

B2

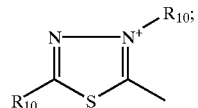

B3

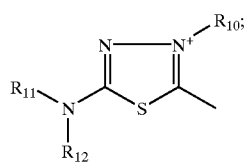

in which $R_{10}$ is chosen from $C_1$–$C_4$ alkyl radicals, and $R_{11}$ and $R_{12}$, which may be identical or different, are chosen from a hydrogen atom and $C_1$–$C_4$ alkyl radicals;

(III)

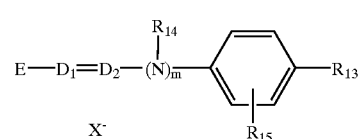

(III')

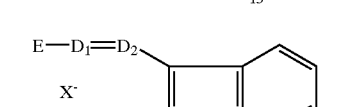

in which formulae (III) and (III'):

$R_{13}$ is chosen from a hydrogen atom, $C_1$–$C_4$ alkoxy radicals, halogen atoms chosen from bromine, chlorine, iodine and fluorine and unsubstituted and substituted amino radicals, $R_{14}$ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals, $R_{15}$ is chosen from a hydrogen atom and halogen atoms chosen from bromine, chlorine, iodine and fluorine, $R_{16}$ and $R_{17}$, which may be identical or different, are chosen from a hydrogen atom and $C_1$–$C_4$ alkyl radicals, $D_1$ and $D_2$, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures below:

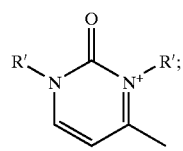

E3

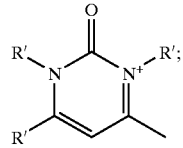

E4

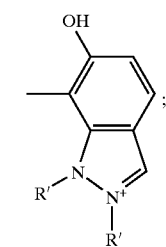

E5

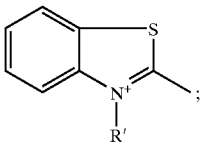

E6

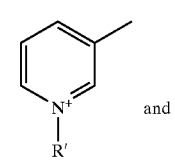

E7 and

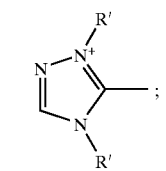

E8 in which R' is chosen from $C_1$–$C_4$ alkyl radicals;

when m is 0 and when $D_1$ is a nitrogen atom, then E can also be a group of structure E9 below:

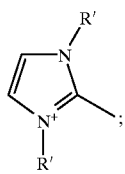

E9 in which R' is chosen from $C_1$–$C_4$ alkyl radicals; and

E in the formula (III') is a group chosen from structures E1 to E8 below;

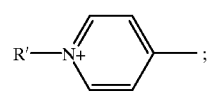

E1

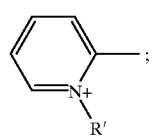

E2

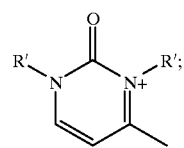

E3

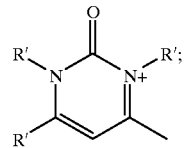

E4

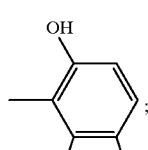

E5

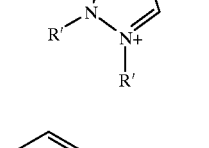

E6

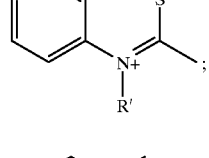

E7 and

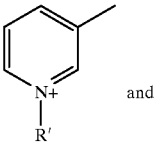

-continued

E8

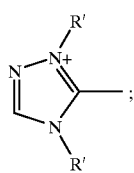

in which R' is chosen from $C_1$–$C_4$ alkyl radicals;
when m is 0 and when $D_1$ is a nitrogen atom, then E can also be a group of structures E9 below;

E9

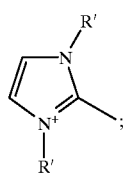

in which R' is chosen from $C_1$–$C_4$ alkyl radicals; and
(ii) at least one compound chosen from polyols and $C_1$–$C_6$ aliphatic ethers of $C_3$–$C_9$ polyols,
   said composition being free of oxidases or oxidoreductases,
   and wherein said at least one cationic direct dye and said at least one compound are present in an amount effective to achieve direct dyeing of said keratin fibers.

34. A composition for the direct dyeing of keratin fibers comprising:
a cationic direct dye of formula (I14)

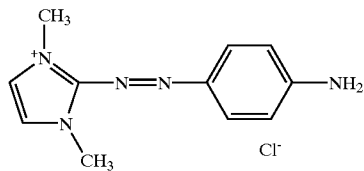

and
propylene glycol.

35. A composition for the first dyeing of keratin fibers comprising:
a cationic direct dye of formula (I1)

(I1)

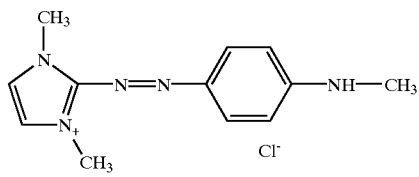

and
propylene glycol monomethyl ether.

36. The composition according to claim 28, wherein $X^-$ is chosen from chloride, methyl sulphate and acetate and wherein for $R^8$ and $R^9$, said halogen atoms are chosen from bromine, chlorine, iodine, and flourine.

37. The composition according to claim 28, wherein said keratin fibers are human keratin fibers.

38. The composition according to claim 37, wherein said human keratin fibers are hair.

39. The composition according to claim 36, wherein said at least one cationic direct dye of formula (I) is chosen from structures (I1) to (I29) and (I31) to (I54) below:

(I1)
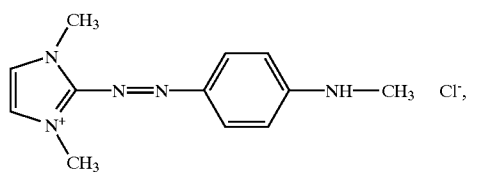

(I2)
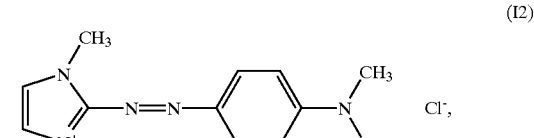

(I3)

(I4)
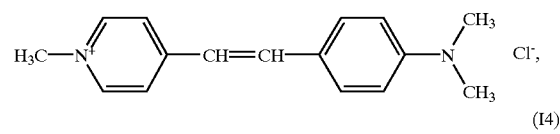

(I5)
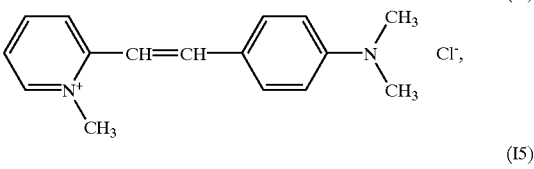

(I6)
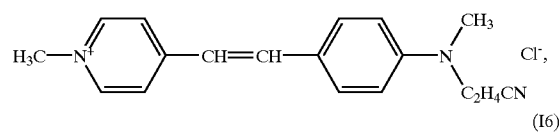

(I7)
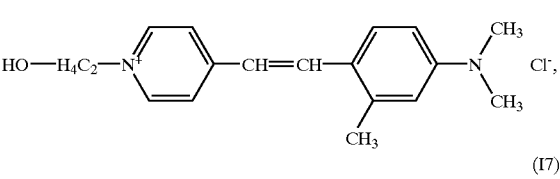

(I8)
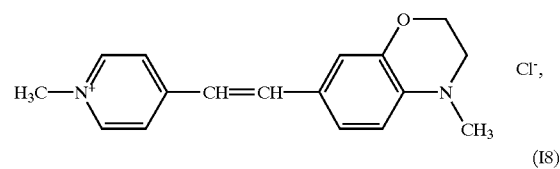

(I9)
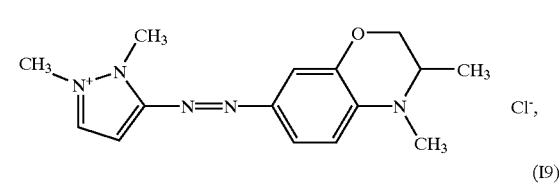

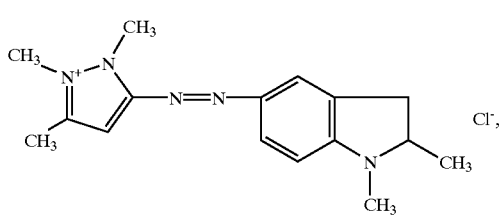

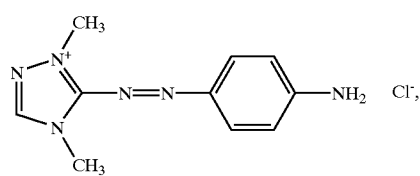 (I10)
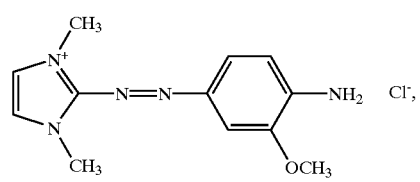 (I11)
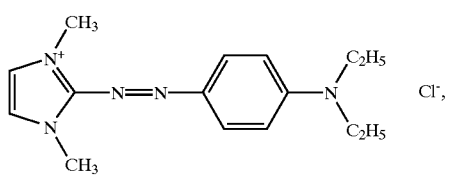 (I12)
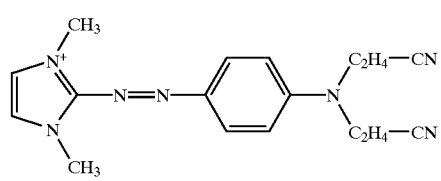 (I13)
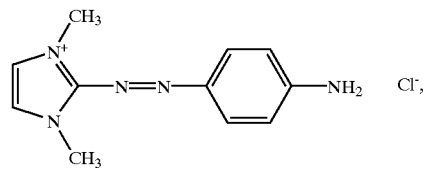 (I14)
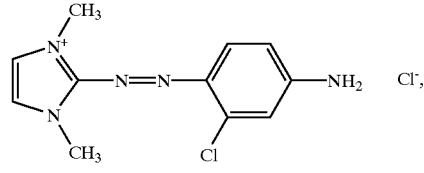 (I15)
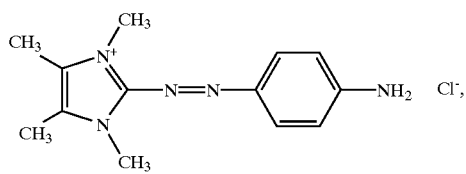 (I16)
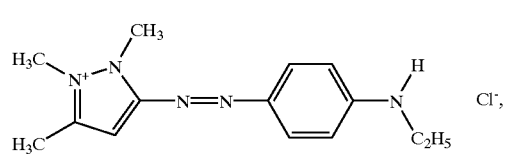 (I17)
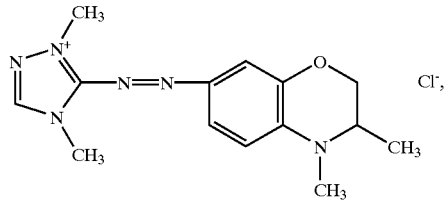 (I18)
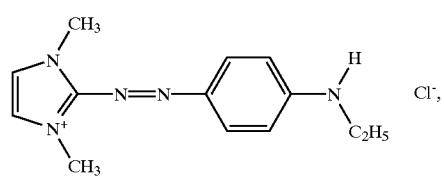 (I19)
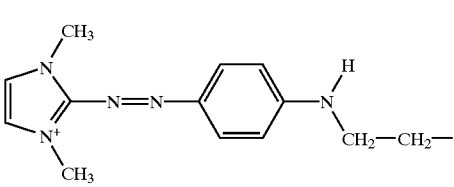 (I20)
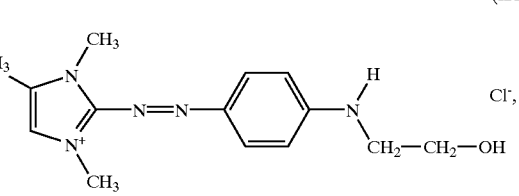 (I21)
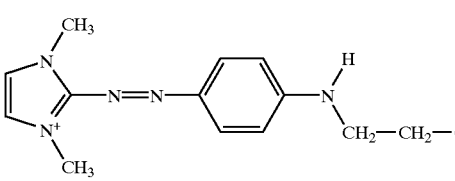 (I22)
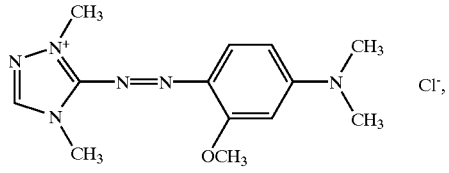 (I23)
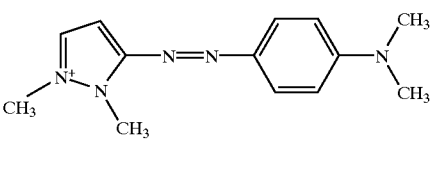 (I24)
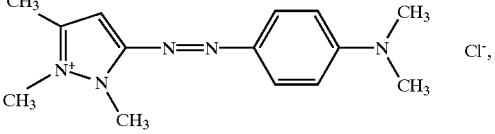 (I25)

-continued
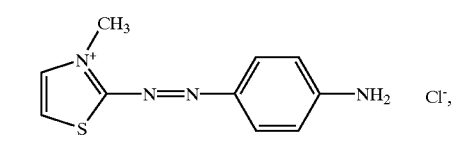 (I26)
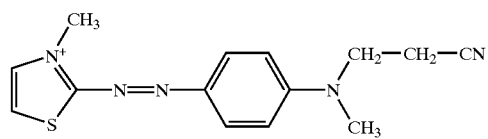 (I27)
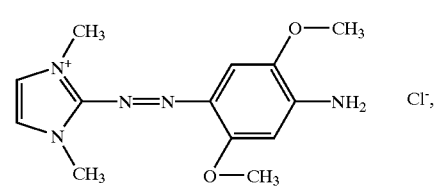 (I28)
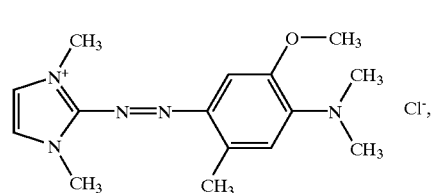 (I29)
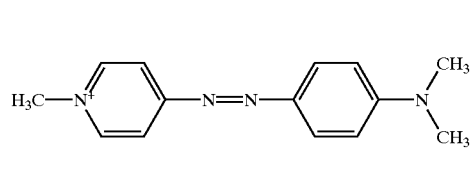 (I30)
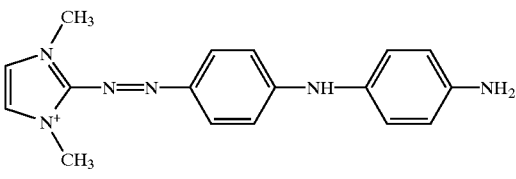 (I31)
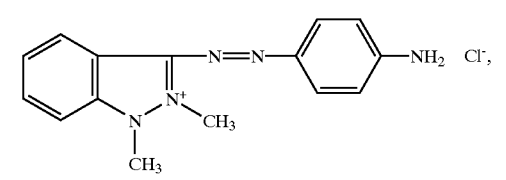 (I32)
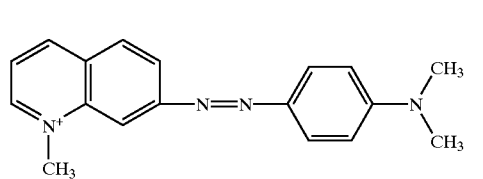 (I33)
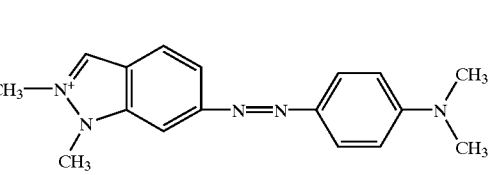 (I34)
-continued
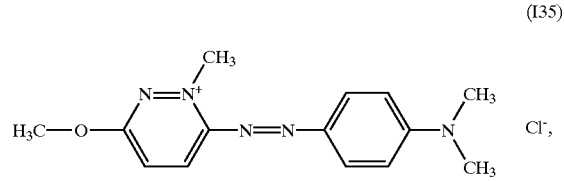 (I35)
 (I36)
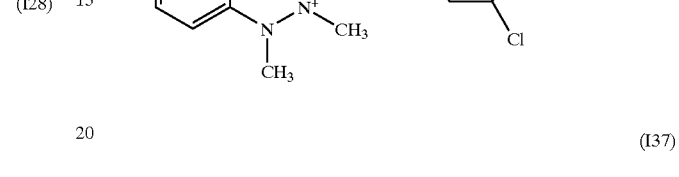 (I37)
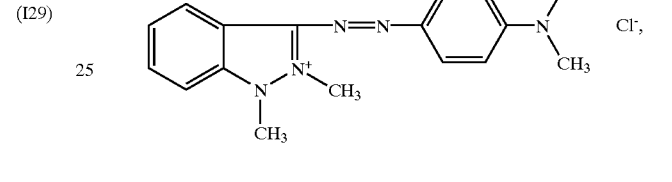 (I38)
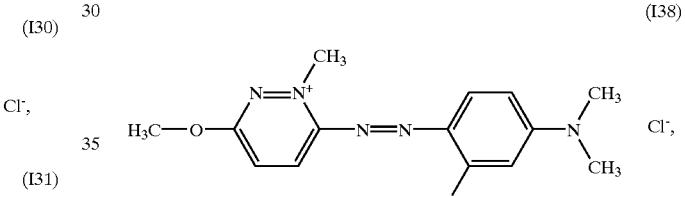 (I39)
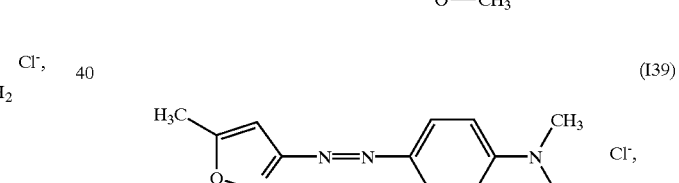 (I40)
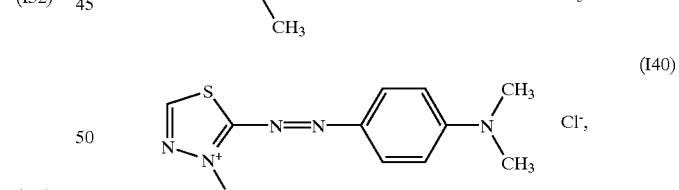 (I41)
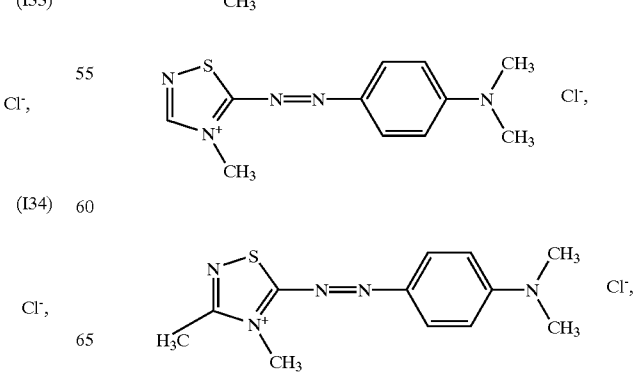 (I42)

(I43)
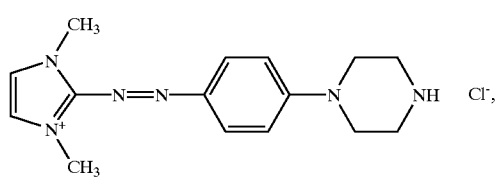
(I44)
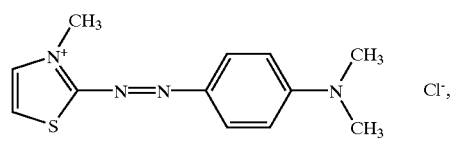
(I45)
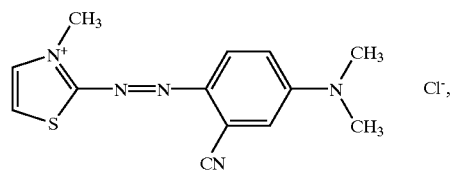
(I46)
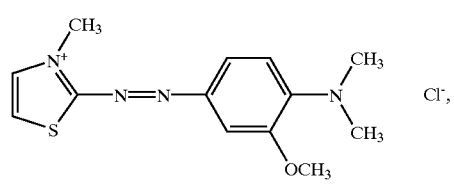
(I47)
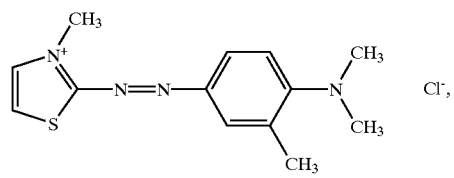
(I48)
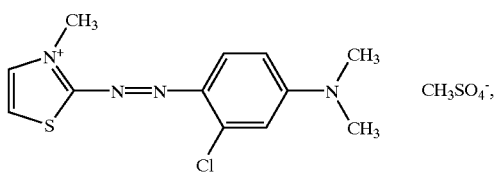
(I49)
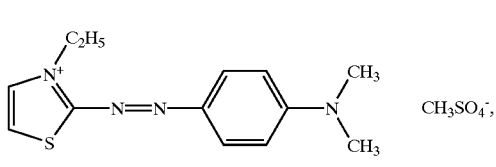
(I50)
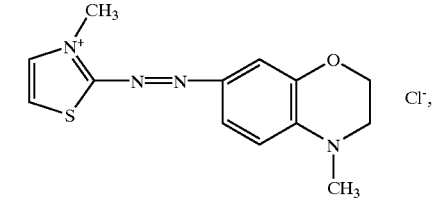
(I51)
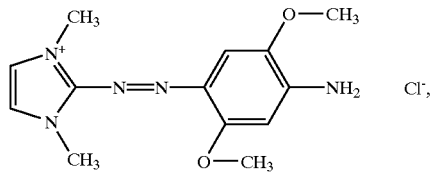
(I52)
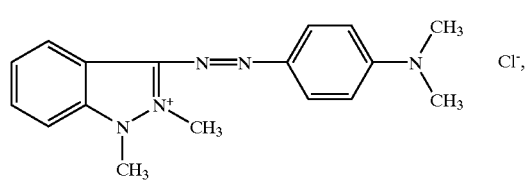
(I53)
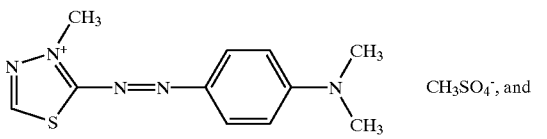
(I54)
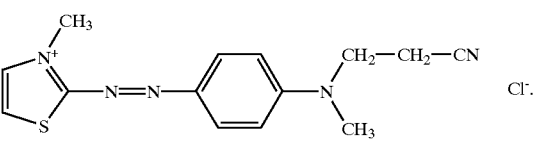
40. The composition according to claim 39, wherein said at least one cationic direct dye is chosen from structures (I1), (I2), (I14) and (I31).
41. The composition according to claim 28, wherein said at least one cationic direct dye of formula (II) is chosen from structures (II1) to (II9) below:
(II1)
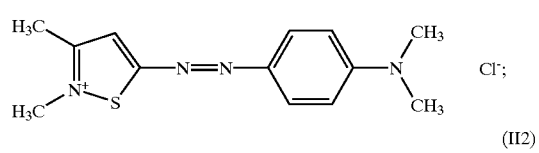
(II2)
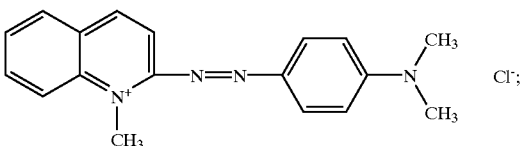
(II3)
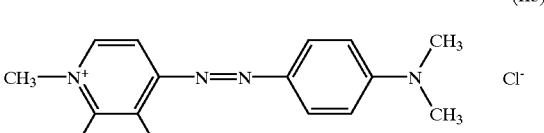

-continued
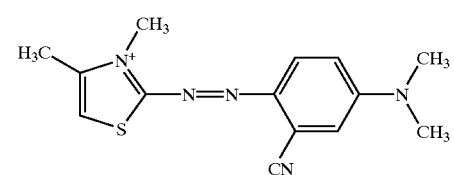 (II4)
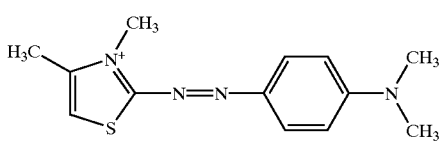 (II5)
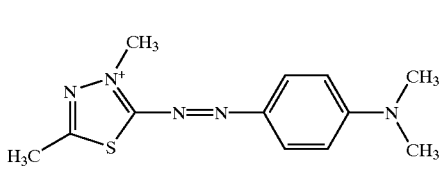 (II6)
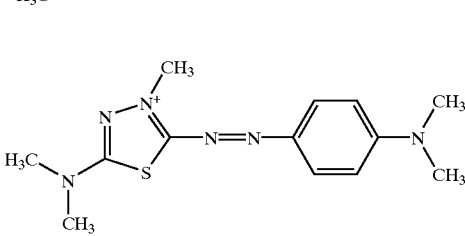 (II7)
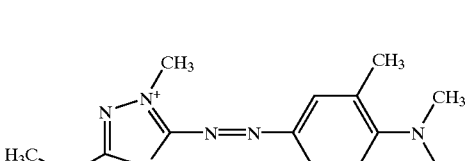 (II8)
and
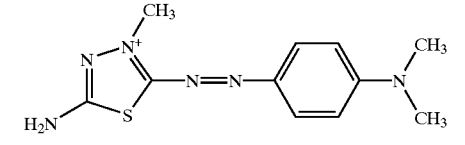 (II9)
42. The composition according to claim 28, wherein said at least one cationic direct dye of formula (III) is chosen from structures (III1) to (III 18) below:
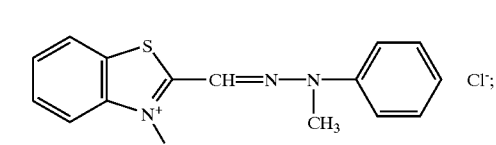 (III1)
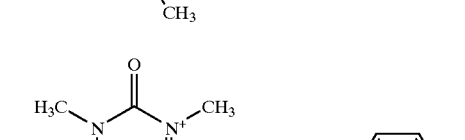 (III2)
-continued
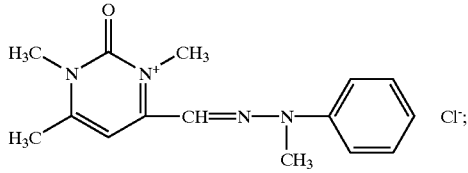 (III3)
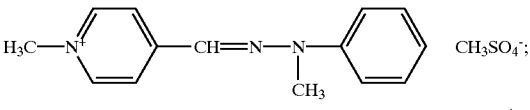 (III4)
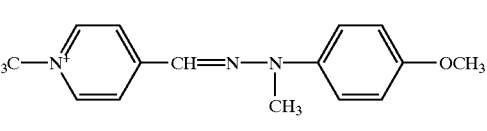 (III5)
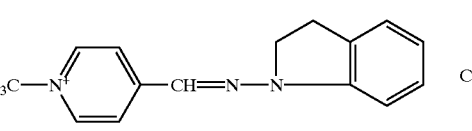 (III6)
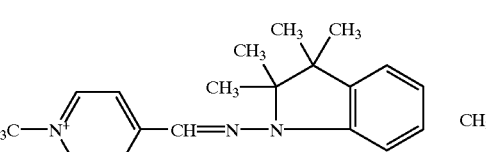 (III7)
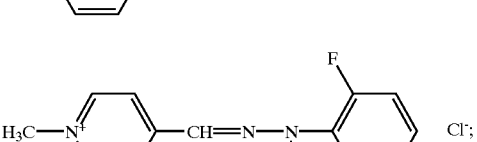 (III8)
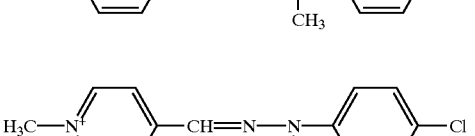 (III9)
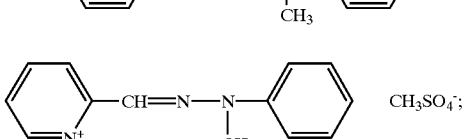 (III10)
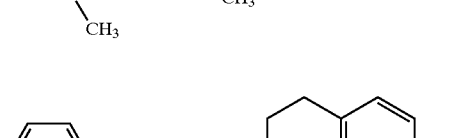 (III11)
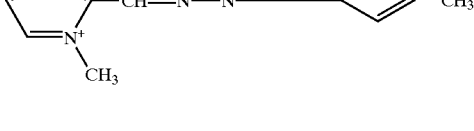 (III12)

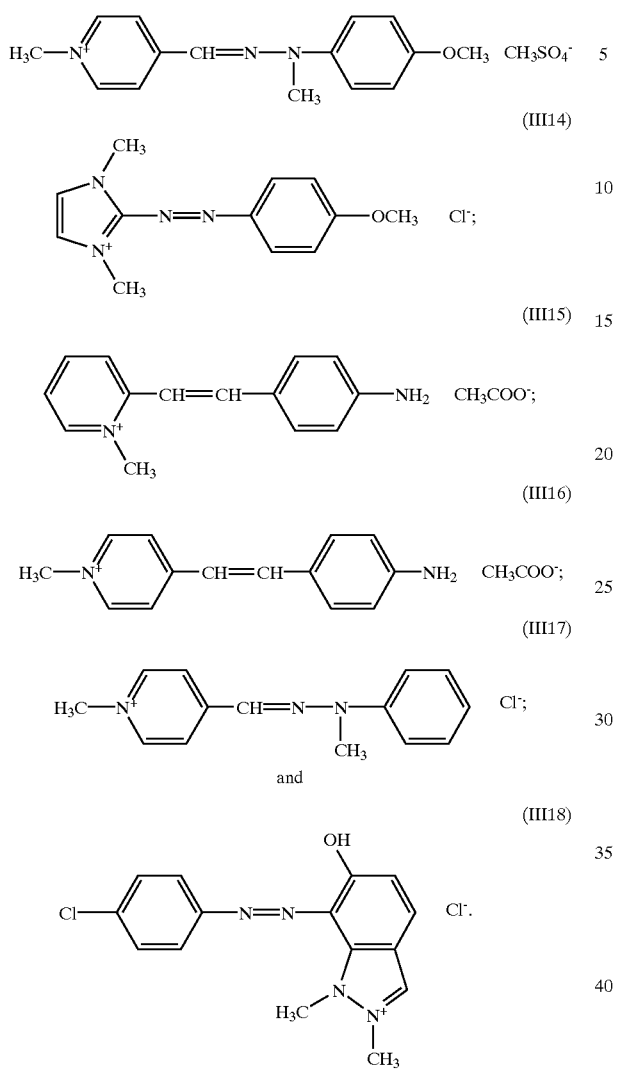

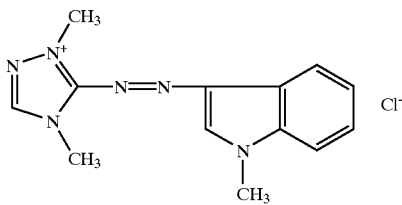

43. The composition according to claim 42, wherein said at least one cationic direct dye of formula (III) is chosen from structures (III4), (III5) and (III13).

44. The composition according to claim 28, wherein said at least one cationic direct dye of formula (III') is chosen from structures (III'1) to (III'3) below:

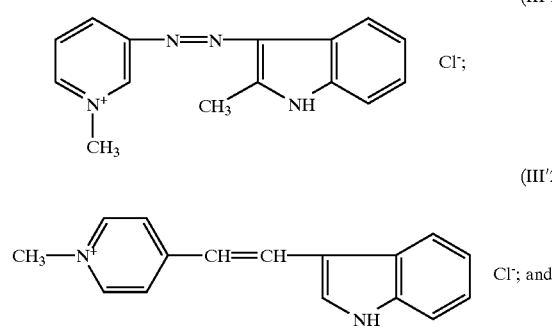

45. The composition according to claim 28, wherein said at least one cationic direct dye is present in an amount ranging from 0.001 to 10% by weight relative to the total weight of the composition.

46. The composition according to claim 45, wherein said at least one cationic direct dye is present in an amount ranging from 0.005 to 5% by weight relative to the total weight of the composition.

47. The composition according to claim 28, wherein said at least one compound is present in an amount ranging from 0.1 to 40% by weight relative to the total weight of the composition.

48. The composition according to claim 47, wherein said at least one compound is present in an amount ranging from 0.5 to 20% by weight relative to the total weight of the composition.

49. The composition according to claim 28, wherein said composition further comprises additional direct dyes.

50. The composition according to claim 28, wherein said composition further comprises water.

51. The composition according to claim 50, wherein said composition further comprises at least one organic solvent other than polyols, $C_1$–$C_8$ aliphatic ethers of $C_3$–$C_9$ polyols, and $C_6$–$C_8$ aromatic ethers of $C_2$–$C_9$ polyols.

52. The composition according to claim 28, wherein said composition has a pH ranging from 2 to 11.

53. The composition according to claim 52, wherein said pH ranges from 5 to 10.

54. A multi-compartment dyeing kit comprising at least two separate compartments wherein a first compartment contains a composition comprising: at least one cationic direct dye chosen from those of formulae (I), (II), (III) and (III') below:

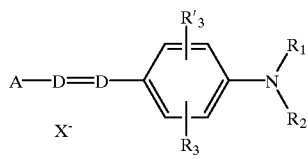

in which formula (I):
D is chosen from a nitrogen atom and a —CH group,
$R_1$ and $R_2$, which may be identical or different, are chosen from a hydrogen atom, $C_1$–$C_4$ alkyl radicals optionally having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals,
$R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, X⁻ is an anion,
A is a group chosen from structures $A_1$ to $A_{18}$ below:
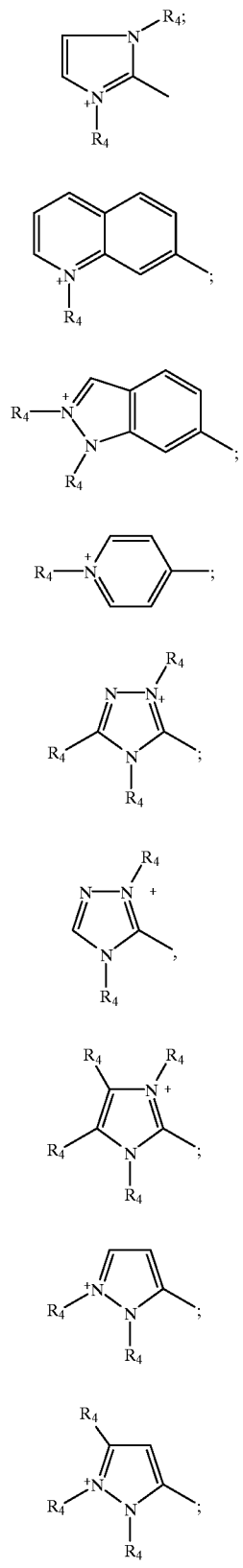
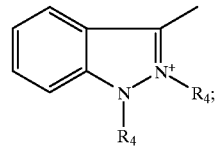
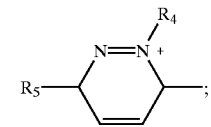
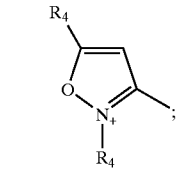
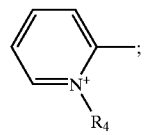
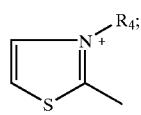
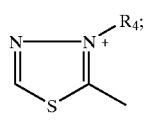
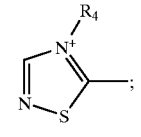
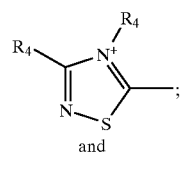
in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

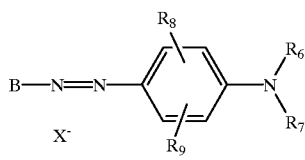
(II)

in which formula (II):

R$_6$ is chosen from a hydrogen atom and C$_1$–C$_4$ alkyl radicals,

R$_7$ is chosen from a hydrogen atom, alkyl radicals having a substituent chosen from —CN and amino radicals, and a 4'-aminophenyl radical, or forms, with R$_6$, a nitrogenous heterocycle optionally oxygenated and optionally having a substituent chosen from C$_1$–C$_4$ alkyl radicals, R$_8$ and R$_9$, which may be identical or different, are chosen from a hydrogen atom, halogen atoms, and C$_1$–C$_4$ alkyl, C$_1$–C$_4$ alkoxy, and —CN radicals, X$^-$ is an anion, B is a group chosen from structures B1 to B6 below:

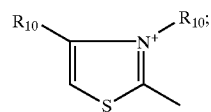 B1

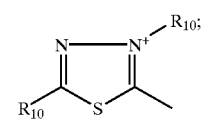 B2

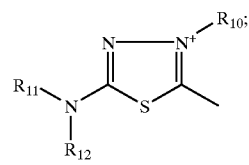 B3

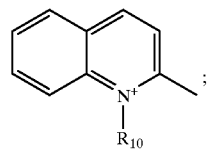 B4

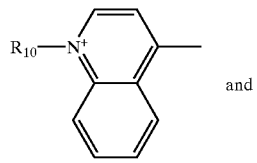 B5 and

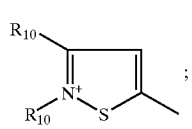 B6 ;

in which R$_{10}$ is chosen from C$_1$–C$_4$ alkyl radicals, and R$_{11}$ and R$_{12}$, which may be identical or different, are chosen from a hydrogen atom and C$_1$–C$_4$ alkyl radicals;

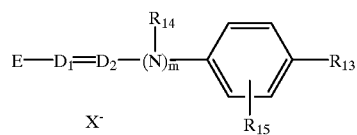
(III)

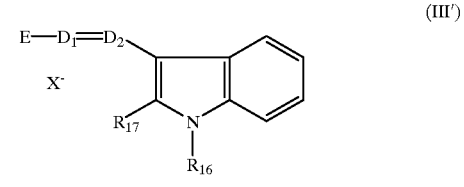
(III')

in which formulae (III) and (III'):

R$_{13}$ is chosen from a hydrogen atom, C$_1$–C$_4$ alkoxy radicals, halogen atoms chosen from bromine, chlorine, iodine and fluorine and unsubstituted and substituted amino radicals, R$_{14}$ is chosen from a hydrogen atom, and C$_1$–C$_4$ alkyl radicals or forms, with a carbon atom of the benzene ring, a heterocycle which is optionally oxygenated and optionally has a substituent chosen from C$_1$–C$_4$ alkyl radicals, R$_{15}$ is chosen from a hydrogen atom and halogen atoms chosen from bromine, chlorine, iodine and fluorine, R$_{16}$ and R$_{17}$, which may be identical or different, are chosen from a hydrogen atom and C$_1$–C$_4$ alkyl radicals, D$_1$ and D$_2$, which may be identical or different, are chosen from a nitrogen atom and a —CH group, m is 0 or 1, it being understood that when R$_{13}$ is an unsubstituted amino radical, then D$_1$ and D$_2$ are simultaneously a —CH group and m is 0, X$^-$ is an anion, E is a group chosen from structures E1 to E8 below:

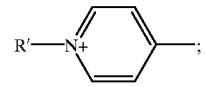 E1

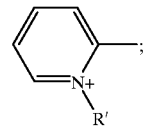 E2

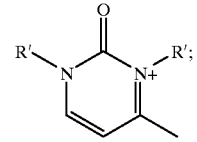 E3

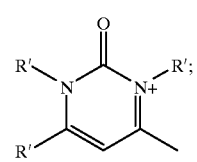 E4

-continued

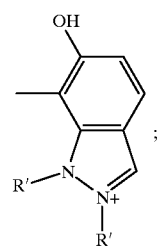
E5

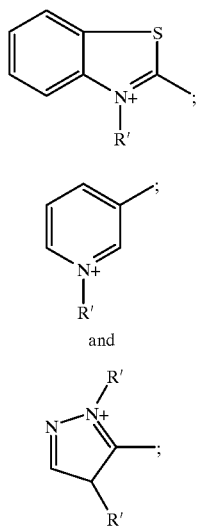
E6

E7 and

E8 in which R' is chosen from C₁–C₄ alkyl radicals;

when m is 0 and when D₁ is a nitrogen atom, then E can also be a group of structure E9 below:

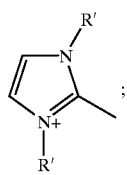
E9 in which R' is chosen from C₁–C₄ alkyl radicals; and a second compartment contains a composition comprising at least one oxidizing agent other than oxidases or oxidoreductases, wherein either the composition in the first compartment or the composition in the second compartment additionally comprises at least one compound chosen from polyols, C₆–C₈ aromatic ethers of C₂–C₉ polyols.

55. A process for the direct dyeing of keratin fibers comprising applying to said fibers, for a period which is sufficient to develop a desired coloration, at least one composition for the direct dyeing of keratin fibers comprising:

(i) at least one cationic direct dye chosen from those of formulae (I), (II), (III) and (III') below:

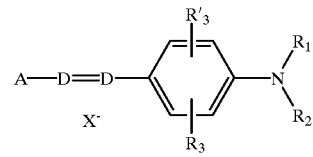
(I)

in which formula (I):

D is chosen from a nitrogen atom and a —CH group,

R₁ and R₂, which may be identical or different, are chosen from a hydrogen atom, C₁–C₄ alkyl radicals having a substituent chosen from —CN, —OH, and —NH₂ radicals, and a 4'-aminophenyl radical; or form, with a carbon atom of the benzene ring, a nitrogenous heterocycle, optionally oxygenated and optionally having at least one substituent chosen from C₁–C₄ alkyl radicals, R₃ and R'₃, which may be identical or different, are chosen from a hydrogen atom, halogen atoms chosen from chlorine, bromine, iodine and fluorine, and cyano, C₁–C₄ alkoxy, C₁–C₄ alkyl, and acetyloxy radicals, X⁻ is an anion, A is a group chosen from structures A₁ to A₁₈ below:

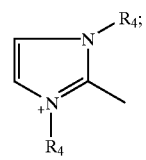
A₁

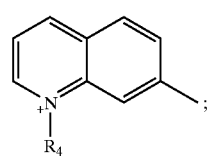
A₂

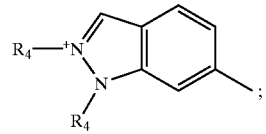
A₃

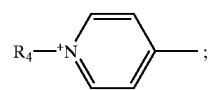
A₄

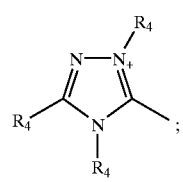
A₅ in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

with the further proviso that when D is a nitrogen atom, $R_1$ and $R_2$ are identically $C_1$–$C_4$ unsibstituted alkyl radicals, and $R_3$ and $R'_3$ are identically or differently chosen from a hydrogen atom, $C_1$–$C_4$ alkoxy, and $C_1$–$C_4$ alkyl, then A cannot be $A_4$ or $A_{13}$;

$$B-N=N-\underset{X^-}{\underset{R_9}{\overset{R_8}{\bigcirc}}}-N\underset{R_7}{\overset{R_6}{<}} \quad (II)$$

in which formula (II):

$R_6$ is chosen from a hydrogen atom and $C_1$–$C_4$ alkyl radicals, $R_7$ is chosen from a hydrogen atom, alkyl radicals having a substituent chosen from —CN and amino radicals, and a 4'-aminophenyl radical, or forms, with $R_6$, a nitrogenous heterocycle optionally oxygenated and optionally having a substituent chosen from $C_1$–$C_4$ alkyl radicals, $R_8$ and $R_9$, which may be identical or different, are chosen from a hydrogen atom, halogen atoms, and $C_1$–$C_4$ alkyl, $C_1$–$C_4$ alkoxy, and —CN radicals, $X^-$ is an anion, B is a group chosen from structures B1 to B6 below:

-continued

B2
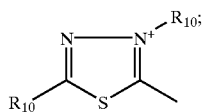

B3
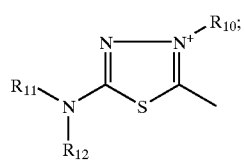

B4
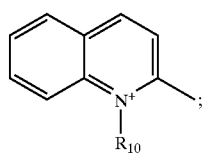

B5
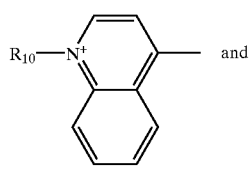 and

B6
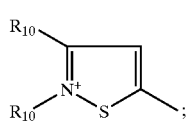

in which $R_{10}$ is chosen from $C_1$–$C_4$ alkyl radicals, and $R_{11}$ and $R_{12}$, which may be identical or different, are chosen from a hydrogen atom and $C_1$–$C_4$ alkyl radicals;

(III)
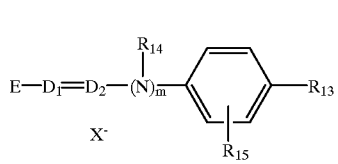

(III')
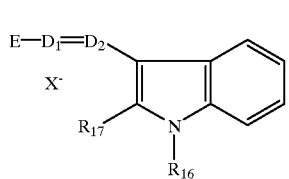

in which formulae (III) and (III'):
$R_{13}$ is chosen from a hydrogen atom, $C_1$–$C_4$ alkoxy radicals, halogen atoms chosen from bromine, chlorine, iodine and fluorine and unsubstituted and substituted amino radicals,
$R_{14}$ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals,
$R_{15}$ is chosen from a hydrogen atom and halogen atoms chosen from bromine, chlorine, iodine and fluorine,
$R_{16}$ and $R_{17}$, which may be identical or different, are chosen from a hydrogen atom and $C_1$–$C_4$ alkyl radicals,
$D_1$ and $D_2$, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

E1
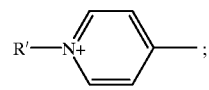

E2
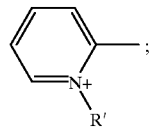

E3
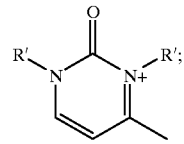

E4
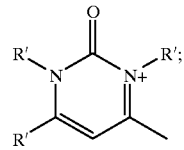

E5
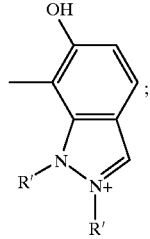

E6
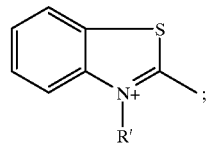

E7
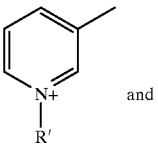 and

E8
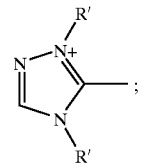

in which R' is chosen from $C_1$–$C_4$ alkyl radicals;
when m is 0 and when $D_1$ is a nitrogen atom, then E can also be a group of structure E9 below:

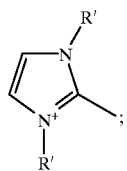
E9 in which R' is chosen from $C_1$–$C_4$ alkyl radicals; with the proviso that, in the formula (III), when $D_1$ and $D_2$ are both nitrogen atoms, m is 0, $R_{13}$ is a dialkyl-substituted amino radical, and $R_{15}$ is a hydrogen atom, then E cannot be $E_1$, $E_2$, or $E_6$; and (ii) at least one compound chosen from polyols, and $C_1$–$C_8$ aliphatic ethers of $C_3$–$C_9$ polyols, said composition being free of oxidases or oxidoreductases, and wherein said at least one cationic dye and said at least one compound are present in an amount effective to achieve direct dyeing of said keratin fibers;

rinsing the fibers, optionally washing said fibers with shampoo, then optionally rinsing again and drying.

56. A process for dyeing keratin fibers according to claim 55, wherein said keratin fibers are human keratin fibers.

57. A process for dyeing keratin fibers according to claim 56, wherein said human keratin fibers are hair.

58. A process for the direct dyeing of keratin fibers according to claim 55, wherein said fibers are not rinsed a second time before drying.

59. A process for the direct dyeing of keratin fibers comprising:

separately storing a first composition comprising (i) at least one cationic direct dye chosen from those of formulae (I), (II), (III) and (III') below:

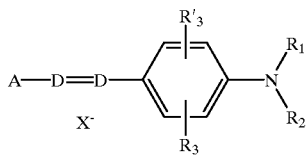
(I)

in which formula (I):

D is chosen from a nitrogen atom and a —CH group, $R_1$ and $R_2$, which may be identical or different, are chosen from a hydrogen atom, $C_1$–$C_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals, $R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, $X^-$ is an anion, A is a group chosen from structures $A_1$ to $A_{18}$ below:

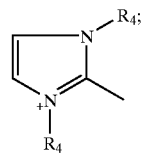
$A_1$

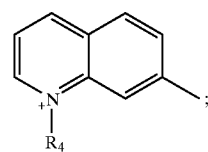
$A_2$

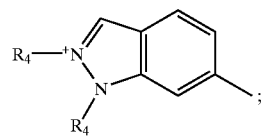
$A_3$

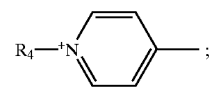
$A_4$

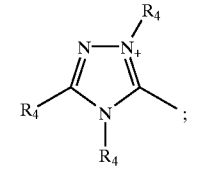
$A_5$

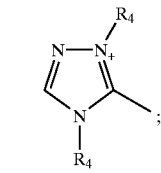
$A_6$

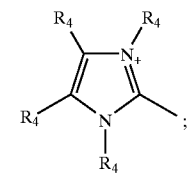
$A_7$

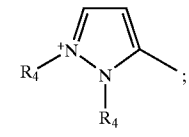
$A_8$

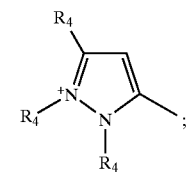
$A_9$

-continued

A10
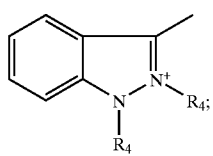

A11
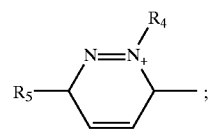

A12
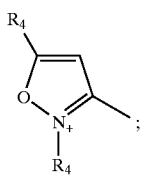

A13
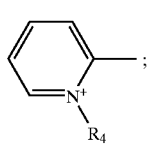

A14
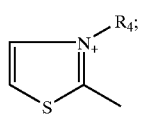

A15
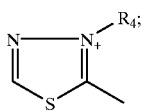

A16
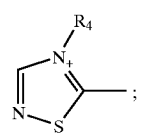

A17
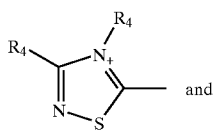 and

A18
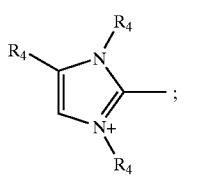

in which $R_4$ is chosen from $C_1$–$C_4$ alkyl radicals which can be substituted with a hydroxyl radical and $R_5$ is chosen from $C_1$–$C_4$ alkoxy radicals, with the proviso that when D is —CH, when A is $A_4$ or $A_{13}$ and when $R_3$ is other than an alkoxy radical, then $R_1$ and $R_2$ are not simultaneously a hydrogen atom;

with the further proviso that when D is a nitrogen atom, $R_1$ and $R_2$ are identically $C_1$–$C_4$ unsubstituted alkyl radicals, and $R_3$ and $R'_3$ are identically or differently chosen from a hydrogen atom, $C_1$–$C_4$ alkoxy, and $C_1$–$C_4$ alkyl, then A cannot be $A_4$ or $A_{13}$;

(II)
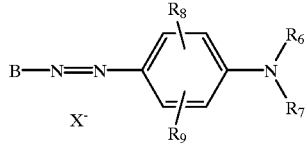

in which formula (II):

$R_6$ is chosen from a hydrogen atom and $C_1$–$C_4$ alkyl radicals, $R_7$ is chosen from a hydrogen atom, alkyl radicals having a substituent chosen from —CN and amino radicals, and a 4'-aminophenyl radical, or forms, with $R_6$, a nitrogenous heterocycle optionally oxygenated and optionally having a substituent chosen from $C_1$–$C_4$ alkyl radicals, $R_8$ and $R_9$, which may be identical or different, are chosen from a hydrogen atom, halogen atoms, and $C_1$–$C_4$ alkyl, $C_1$–$C_4$ alkoxy, and —CN radicals, $X^-$ is an anion, B is a group chosen from structures B1 to B6 below:

B1
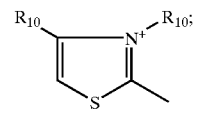

B2
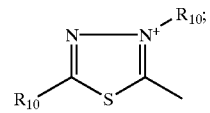

B3
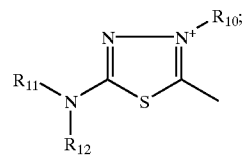

B4
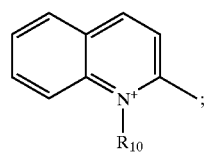

B5
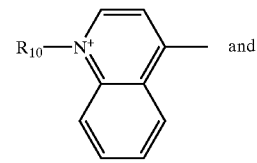 and

B6
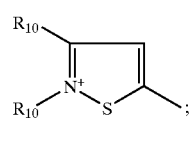

in which $R_{10}$ is chosen from $C_1$–$C_4$ alkyl radicals, and $R_{11}$ and $R_{12}$, which may be identical or different, are chosen from a hydrogen atom and $C_1$–$C_4$ alkyl radicals;

(III)
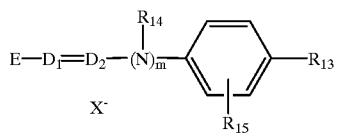

(III')
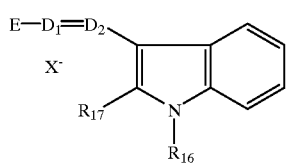

in which formulae (III) and (III'):

$R_{13}$ is chosen from a hydrogen atom, $C_1$–$C_4$ alkoxy radicals, halogen atoms chosen from bromine, chlorine, iodine and fluorine and unsubstituted and substituted amino radicals, $R_{14}$ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals, $R_{15}$ is chosen from a hydrogen atom and halogen atoms chosen from bromine, chlorine, iodine and fluorine, $R_{16}$ and $R_{17}$, which may be identical or different, are chosen from a hydrogen atom and $C_1$–$C_4$ alkyl radicals, $D_1$ and $D_2$, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

E1
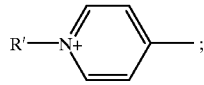

E2
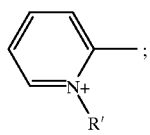

E3
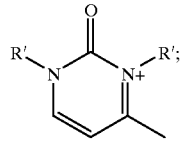

E4
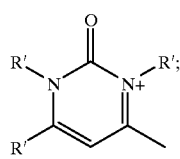

-continued

E5
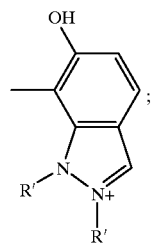

E6
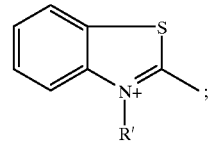

E7
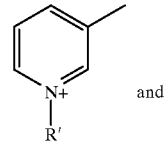 and

E8
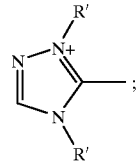

in which R' is chosen from $C_1$–$C_4$ alkyl radicals;

when m is 0 and when $D_1$ is a nitrogen atom, then E can also be a group of structure E9 below:

E9
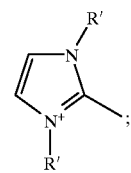

in which R' is chosen from $C_1$–$C_4$ alkyl radicals;

with the proviso that, in the formula (III), when $D_1$ and $D_2$ are both nitrogen atoms, m is 0, $R_{13}$ is a dialkyl-substituted amino radical, and $R_{15}$ is a hydrogen atom, then E cannot be $E_1$, $E_2$, or $E_6$; and separately storing a second composition comprising at least one oxidizing agent other than oxidases or oxidoreductases and thereafter mixing said first composition with said second composition and applying this mixture to said keratin fibers, wherein said first and second composition additionally comprises at least one compound chosen from polyols and $C_1$–$C_8$ aliphatic ethers of $C_3$–$C_9$ polyols, and wherein said at least one cationic direct dye and said at least one compound are present in an amount effective to achieve direct dyeing of said keratin fibers.

60. A multi-compartment dyeing kit comprising at least two separate compartments wherein a first compartment contains a composition comprising: at least one cationic direct dye chosen from those of formulae (I), (II), (III) and (III') below:

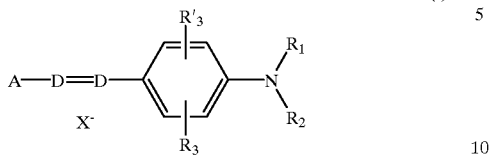
(I)

in which formula (I):

D is chosen from a nitrogen atom and a —CH group, $R_1$ and $R_2$, which may be identical or different, are chosen from a hydrogen atom, $C_1$–$C_4$ alkyl radicals having a substituent chosen from —CN, —OH, and —NH$_2$ radicals, and a 4'-aminophenyl radical; or form, with a carbon atom of the benzene ring, a nitrogenous heterocycle, optionally oxygenated and optionally having at least one substituent chosen from $C_1$–$C_4$ alkyl radicals, $R_3$ and $R'_3$, which may be identical or different, are chosen from a hydrogen atom, halogen atoms chosen from chlorine, bromine, iodine and fluorine, and cyano, $C_1$–$C_4$ alkoxy, $C_1$–$C_4$ alkyl, and acetyloxy radicals, X⁻ is an anion, A is a group chosen from structures $A_1$ to $A_{18}$ below:

$A_1$
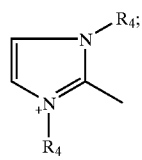

$A_2$
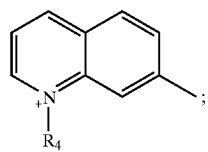

$A_3$
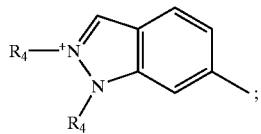

$A_4$
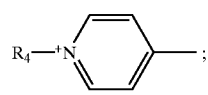

$A_5$
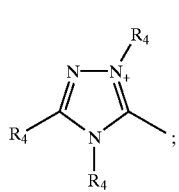

-continued $A_6$
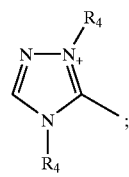

$A_7$
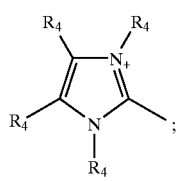

$A_8$
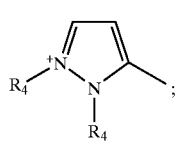

$A_9$
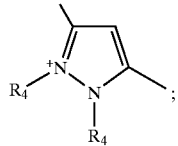

$A_{10}$
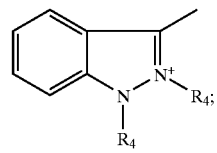

$A_{11}$
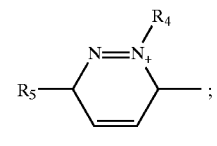

$A_{12}$
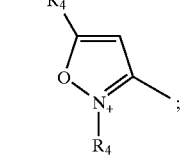

$A_{13}$
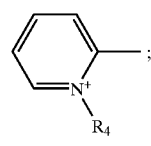

$A_{14}$
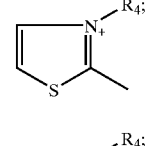

$A_{15}$
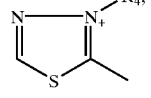

-continued

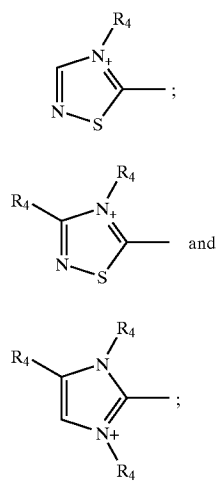

A16

A17

A18 in which R₄ is chosen from $C_1$–$C_4$ alkyl radicals which can be substituted with a hydroxyl radical and R₅ is chosen from $C_1$–$C_4$ alkoxy radicals, with the proviso that when D is —CH, when A is A₄ or A₁₃ and when R₃ is other than an alkoxy radical, then R₁ and R₂ are not simultaneously a hydrogen atom;

with the further proviso that when D is a nitrogen atom, R₁ and R₂ are identically $C_1$–$C_4$ unsubstantiated alkyl radicals, and R₃ and R'₃ are identically or differently chosen from a hydrogen atom, $C_1$–$C_4$ alkoxy, and $C_1$–$C_4$ alkyl, then A cannot be A₄ or A₁₃;

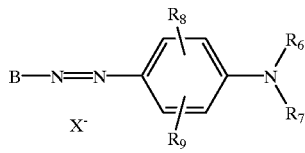

(II)

in which formula (II):

R₆ is chosen from a hydrogen atom and $C_1$–$C_4$ alkyl radicals,

R₇ is chosen from a hydrogen atom, alkyl radicals having a substituent chosen from —CN and amino radicals, and a 4'-aminophenyl radical, or forms, with R₆, a nitrogenous heterocycle optionally oxygenated and optionally having a substituent chosen from $C_1$–$C_4$ alkyl radicals, R₈ and R₉, which may be identical or different, are chosen from a hydrogen atom, halogen atoms, and $C_1$–$C_4$ alkyl, $C_1$–$C_4$ alkoxy, and —CN radicals, X⁻ is an anion, B is a group chosen from structures B1 to B6 below:

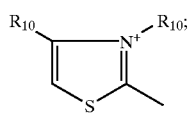

B1

-continued

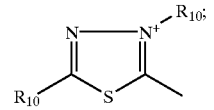

B2

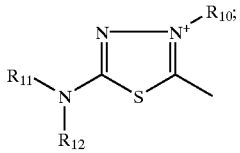

B3

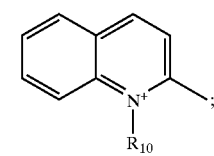

B4

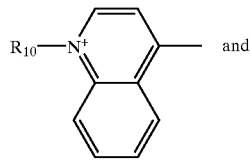

B5

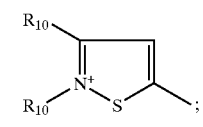

B6 in which R₁₀ is chosen from $C_1$–$C_4$ alkyl radicals, and R₁₁ and R₁₂, which may be identical or different, are chosen from a hydrogen atom and $C_1$–$C_4$ alkyl radicals;

(III)

(III')

in which formulae (III) and (III'):

R₁₃ is chosen from a hydrogen atom, $C_1$–$C_4$ alkoxy radicals, halogen atoms chosen from bromine, chlorine, iodine and fluorine and unsubstituted and substituted amino radicals, R₁₄ is chosen from a hydrogen atom, and $C_1$–$C_4$ alkyl radicals or forms, with a carbon atom of the benzene ring, a heterocycle which is optionally oxygenated and optionally has a substituent chosen from $C_1$–$C_4$ alkyl radicals, R₁₅ is chosen from a hydrogen atom and halogen atoms chosen from bromine, chlorine, iodine and fluorine, R₁₆ and R₁₇, which may be identical or different, are chosen from a hydrogen atom and $C_1$–$C_4$ alkyl radicals, D₁ and D₂, which may be identical or different, are chosen from a nitrogen atom and a —CH group, m is 0 or 1, it being understood that when $R_{13}$ is an unsubstituted amino radical, then $D_1$ and $D_2$ are simultaneously a —CH group and m is 0, $X^-$ is an anion, E is a group chosen from structures E1 to E8 below:

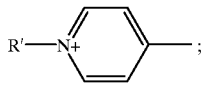   E1

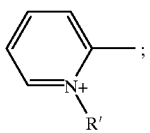   E2

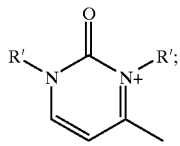   E3

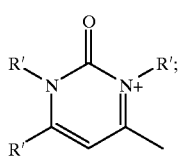   E4

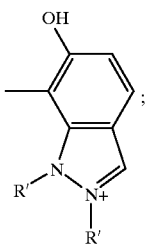   E5

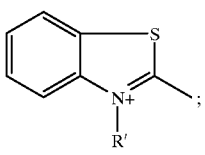   E6

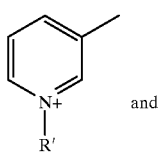 and   E7

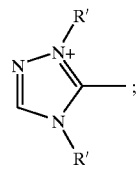   E8 in which R' is chosen from $C_1$–$C_4$ alkyl radicals;

when m is 0 and when $D_1$ is a nitrogen atom, then E can also be a group of structure E9 below:

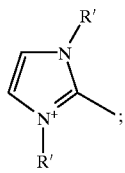   E9 in which R' is chosen from $C_1$–$C_4$ alkyl radicals;

with the proviso that, in the formula (III), when $D_1$ and $D_2$ are both nitrogen atoms, m is 0, $R_{13}$ is a dialkyl-substituted amino radical, and $R_{15}$ is a hydrogen atom, then E cannot be $E_1$, $E_2$, or $E_6$; and a second compartment contains a composition comprising at least one oxidizing agent other than oxidases or oxidoreductases, wherein either the composition in the first compartment or the composition in the second compartment additionally comprises at least one compound chosen from polyols and $C_1$–$C_8$ aliphatic ethers of $C_3$–$C_9$ polyols.

* * * * *

UNITED STATES PATENT AND TRADEMARK OFFICE
CERTIFICATE OF CORRECTION

PATENT NO.  : 6,436,153 B2
DATED       : August 20, 2002
INVENTOR(S) : Christine Rondeau It is certified that error appears in the above-identified patent and that said Letters Patent is hereby corrected as shown below:

Column 20,
Line 55, after "alkyl radicals", insert -- optionally --.

Column 23,
Line 14, after "alkyl radicals", insert -- optionally --.

Column 25,
Line 56, "acieve" should read -- achieve --.
Line 57, "wherein X" should read -- wherein X⁻ --.

Column 35,
In the structure (III11):

" (III11) "

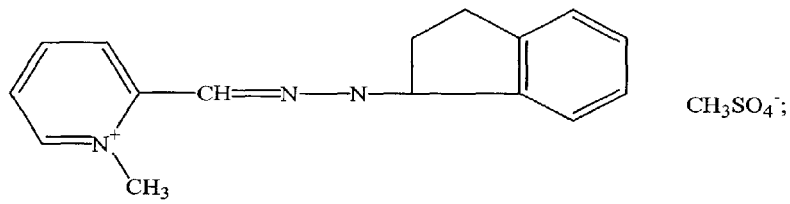

should read

-- (III11)

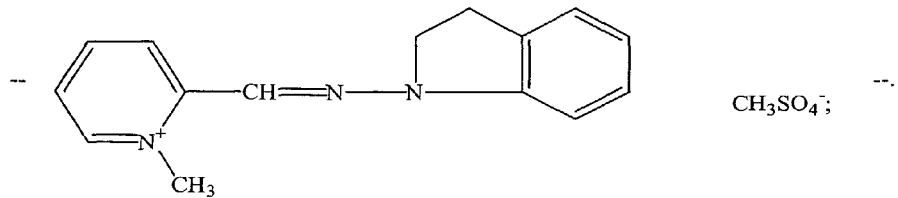

--.

UNITED STATES PATENT AND TRADEMARK OFFICE
CERTIFICATE OF CORRECTION

PATENT NO.   : 6,436,153 B2
DATED        : August 20, 2002
INVENTOR(S)  : Christine Rondeau It is certified that error appears in the above-identified patent and that said Letters Patent is hereby corrected as shown below:

Column 36,
Line 38, "claim 1m" should read -- claim 1, --.
Line 54, after "accordingly", insert -- to --.
Line 60, "claim 1" should read -- claim 28 --.
Line 63, "fibersm" should read -- fibers, --.
Line 65, "comprising" should read -- comprising: --.

Column 37,
Line 15, after "alkyl radicals", insert -- optionally --.

Column 39,
Line 48, after "alkyl radicals", insert -- optionally --.

Column 42,
Line 12, after "alkyl radicals;", insert -- and --.
Line 20, "wherin" should read -- wherein --; and after "cationic", insert -- direct --.
Line 36, "comprising:" should read -- comprising --.
Line 55, after "alkyl radicals", insert -- optionally --.

Column 48,
Line 18, after "alkyl radicals", insert -- optionally --.

Column 50,
Line 28, after "hydrogen atom;", insert the following paragraph:
-- with the further proviso that when D is a nitrogen atom, $R_1$ and $R_2$ are identically $C_1$-$C_4$ unsubstituted alkyl radicals, and $R_3$ and $R'_3$ are identically or differently chosen from a hydrogen atom, $C_1$-$C_4$ alkoxy, and $C_1$-$C_4$ alkyl, then A cannot be $A_4$ or $A_{13}$; --.
Line 43, after "alkyl radicals", insert -- optionally --.

Column 53,
Line 11, after "alkyl radicals;", insert the following paragraph:
-- with the proviso that, in the formula (III), when $D_1$ and $D_2$ are both nitrogen atoms, m is 0, $R_{13}$ is dialkyl-substituted amino radical, and $R_{15}$ is a hydrogen atom, then E cannot be $E_1$, $E_2$, or $E_6$; --.
Line 12, "$C_6$-$C_8$ aromatic" should read -- polyols and $C_1$-$C_8$ aliphatic --.
Line 13, "$C_2$-$C_9$ polyols," should read -- $C_3$-$C_9$ polyols, --.
Line 18, "acieve" should read -- achieve --.
Line 19, before "polyols", delete "$C_1$-$C_8$ aliphatic ethers of $C_3$-$C_9$".

UNITED STATES PATENT AND TRADEMARK OFFICE
CERTIFICATE OF CORRECTION

PATENT NO. : 6,436,153 B2
DATED : August 20, 2002
INVENTOR(S) : Christine Rondeau It is certified that error appears in the above-identified patent and that said Letters Patent is hereby corrected as shown below:

Column 53 cont'd,
Lines 20-25, delete "propylene glycol monomethyl ether, propylene glycol monoethyl ether, isopropylene glycol dimethyl ether, diethylene glycol, monoethyl ether, diethylene glycol monoethyl ether, dipropylene glycol monomethyl ether, tripropylene glycol monomethyl ether and diethylene glycol dimethyl ether." and insert therefor -- $C_2$-$C_9$ polyols and polyalkylene glycols. --.
Lines 41-42, "triporopylene" should read -- tripropylene --.
Line 61, after "alkyl radicals", insert -- optionally --.

Column 54,
Delete structures $A_1$, $A_4$, $A_7$, and $A_8$.

Column 55,
Delete structures $A_9$, $A_{10}$, $A_{13}$, $A_{14}$, and $A_{18}$.
After the semicolon after structure $A_{16}$, insert -- and --.
After the semicolon after structure $A_{17}$, delete "and".

Column 56,
Line 17, after "alky radicals", insert -- optionally --.

Column 57,
Line 18, after "E" and before "is a group", insert -- in the formula (III) --.
Delete structure E6.

Column 58,
Line 16, "below;" should read -- below: --.

Column 59,
Line 13, "structures E9 below;" should read -- structure E9 below: --.
Line 24, "$C_1$-$C_6$" should read -- $C_1$-$C_8$ --.
Line 45, "first dyeing" should read -- direct dyeing --.
Line 60, "X̄is" should read -- X⁻ is --.
Line 62, "$R^8$ and $R^9$," should read -- $R_8$ and $R_9$, --.
Line 63, "flourine" should read -- fluorine --.

UNITED STATES PATENT AND TRADEMARK OFFICE
CERTIFICATE OF CORRECTION

PATENT NO. : 6,436,153 B2
DATED : August 20, 2002
INVENTOR(S) : Christine Rondeau It is certified that error appears in the above-identified patent and that said Letters Patent is hereby corrected as shown below:

<u>Column 63,</u>
Delete structure (I30).
In the structure (I31):

" (I31) "

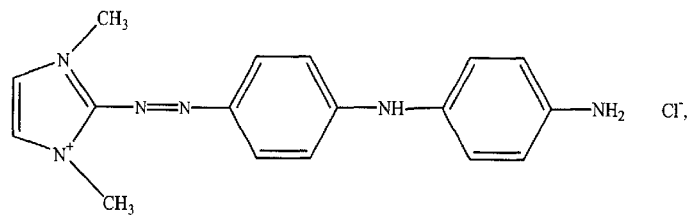

Cl⁻, should read (I31)

-- 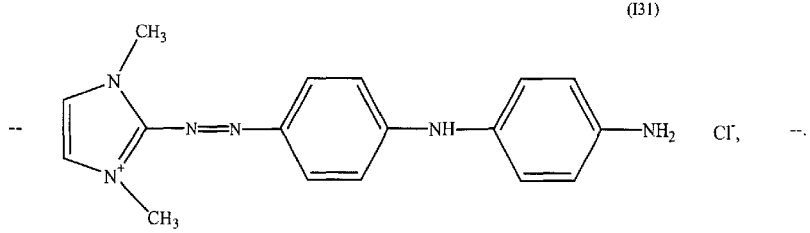 Cl⁻, --.

UNITED STATES PATENT AND TRADEMARK OFFICE
CERTIFICATE OF CORRECTION

PATENT NO.     : 6,436,153 B2
DATED          : August 20, 2002
INVENTOR(S)    : Christine Rondeau It is certified that error appears in the above-identified patent and that said Letters Patent is hereby corrected as shown below:

Column 68,
In the structure (III11):

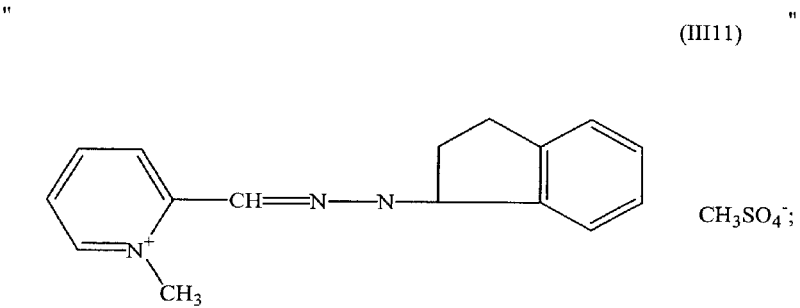

should read

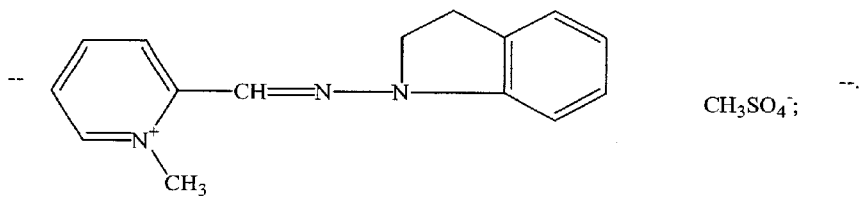

Column 71,
After the structure A6, change the comma to a semicolon.

Column 73,
Line 14, after "alkyl radicals", insert -- optionally --.
Line 66, "$R_{11}$and" should read -- $R_{11}$ and --.

UNITED STATES PATENT AND TRADEMARK OFFICE
CERTIFICATE OF CORRECTION

PATENT NO. : 6,436,153 B2
DATED : August 20, 2002
INVENTOR(S) : Christine Rondeau It is certified that error appears in the above-identified patent and that said Letters Patent is hereby corrected as shown below:

Column 75,
In the structure E8:

"                              "

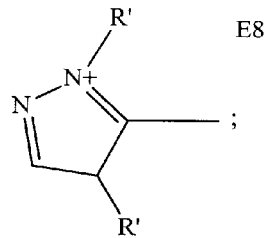

should read

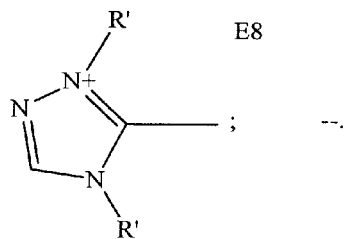

-- ;  --.

Line 58, after "chosen from", delete "polyols,".
Line 61, after "keratin fibers", insert a comma.

Column 76,
Line 18, after "alkyl radicals", insert -- optionally --.

Column 78,
Line 31, "unsibstituted" should read -- unsubstituted --.
Line 49, after "alkyl radicals", insert -- optionally --.

UNITED STATES PATENT AND TRADEMARK OFFICE
CERTIFICATE OF CORRECTION

PATENT NO. : 6,436,153 B2
DATED : August 20, 2002
INVENTOR(S) : Christine Rondeau It is certified that error appears in the above-identified patent and that said Letters Patent is hereby corrected as shown below:

Column 81,
Line 17, after "chosen from polyols", delete the comma.
Line 54, after "alkyl radicals", insert -- optionally --.

Column 83,
After the structure $A_{17}$ and before "and", insert a semicolon.

Column 84,
Line 15, after "alkyl radicals", insert -- optionally --.

Column 86,
Line 59, "first and second composition" should read -- first or said second composition --.

Column 87,
Line 19, after "alkyl radicals", insert -- optionally --.

Column 89,
After the structure $A_{17}$ and before "and", insert a semicolon.
Line 31, "unsubstantiated" should red -- unsubstituted --.
Line 49, after "alkyl radicals", insert -- optionally --.

Signed and Sealed this

Twentieth Day of May, 2003

JAMES E. ROGAN
*Director of the United States Patent and Trademark Office*